(12) United States Patent
Zhang et al.

(10) Patent No.: US 7,919,269 B2
(45) Date of Patent: Apr. 5, 2011

(54) WHITEFLY ECDYSONE RECEPTOR NUCLEIC ACIDS, POLYPEPTIDES, AND USES THEREOF

(75) Inventors: Jianzhong Zhang, Wilimington, DE (US); Dean Ervin Cress, Blacksburg, VA (US); Subba Reddy Palli, Lexington, KY (US); Tarlochan Singh Dhadialla, Indianapolis, IN (US)

(73) Assignee: Intrexon Corporation, Blacksburg, VA (US)

(*) Notice: Subject to any disclaimer, the term of this patent is extended or adjusted under 35 U.S.C. 154(b) by 1098 days.

(21) Appl. No.: 10/490,976

(22) PCT Filed: Feb. 20, 2002

(86) PCT No.: PCT/US02/05234
§ 371 (c)(1),
(2), (4) Date: Mar. 25, 2004

(87) PCT Pub. No.: WO03/027266
PCT Pub. Date: Apr. 3, 2003

(65) Prior Publication Data
US 2004/0235097 A1 Nov. 25, 2004
US 2008/0268499 A9 Oct. 30, 2008

Related U.S. Application Data

(60) Provisional application No. 60/325,534, filed on Sep. 26, 2001.

(51) Int. Cl.
C12N 5/10 (2006.01)
C12N 15/63 (2006.01)
C12N 15/12 (2006.01)

(52) U.S. Cl. .................... 435/69.1; 435/320.1; 435/325; 536/23.5

(58) Field of Classification Search .................. None
See application file for complete search history.

(56) References Cited

U.S. PATENT DOCUMENTS

| | | | |
|---|---|---|---|
| 4,631,211 A | 12/1986 | Houghten |
| 4,859,609 A | 8/1989 | Dull et al. |
| 4,981,784 A | 1/1991 | Evans et al. |
| 4,985,461 A | 1/1991 | Hsu et al. |
| 5,010,175 A | 4/1991 | Rutter et al. |
| 5,117,057 A | 5/1992 | Hsu et al. |
| 5,225,443 A | 7/1993 | Murphy et al. |
| 5,283,173 A | 2/1994 | Fields et al. |
| 5,378,726 A | 1/1995 | Yanagi et al. |
| 5,459,127 A | 10/1995 | Felgner et al. |
| 5,514,578 A | 5/1996 | Hogness et al. |
| 5,530,028 A | 6/1996 | Lidert et al. |
| 5,710,004 A | 1/1998 | Evans et al. |
| 5,723,329 A | 3/1998 | Mangelsdorf et al. |
| 5,880,333 A | 3/1999 | Goff et al. |
| 6,013,836 A | 1/2000 | Hsu et al. |
| 6,096,787 A | 8/2000 | Evans et al. |
| 6,245,531 B1 | 6/2001 | Hogness et al. |
| 6,265,173 B1 | 7/2001 | Evans et al. |
| 6,281,330 B1 | 8/2001 | Evans et al. |
| 6,333,318 B1 | 12/2001 | Evans et al. |
| 6,379,945 B1 | 4/2002 | Jepson et al. |
| 6,458,926 B1 | 10/2002 | Evans et al. |
| 7,119,077 B1 | 10/2003 | Evans et al. |
| 6,723,531 B2 | 4/2004 | Evans et al. |
| 6,756,491 B2 | 6/2004 | Evans et al. |
| 6,958,236 B2 | 10/2005 | Pascal et al. |
| 7,038,022 B1 | 5/2006 | Evans et al. |
| 7,045,315 B2 | 5/2006 | Evans et al. |
| 7,057,015 B1 | 6/2006 | Gage et al. |
| 7,091,038 B2 | 8/2006 | Palli et al. |
| 7,563,879 B2 | 7/2009 | Palli |
| 2002/0110861 A1 | 8/2002 | Dhadialla et al. |
| 2002/0119521 A1 | 8/2002 | Palli et al. |
| 2004/0033600 A1 | 2/2004 | Palli et al. |
| 2004/0096942 A1 * | 5/2004 | Kapitskaya et al. ......... 435/69.1 |
| 2004/0197861 A1 | 10/2004 | Palli |
| 2004/0235097 A1 | 11/2004 | Zhang et al. |
| 2005/0266457 A1 | 12/2005 | Palli et al. |
| 2006/0100416 A1 | 5/2006 | Palli et al. |
| 2008/0051344 A1 | 2/2008 | Palli et al. |
| 2008/0064097 A1 | 3/2008 | Palli |
| 2008/0214790 A1 | 9/2008 | Palli |
| 2008/0280321 A9 | 11/2008 | Palli |

FOREIGN PATENT DOCUMENTS

| | | |
|---|---|---|
| EP | 234994 A1 | 9/1987 |
| EP | 461809 A1 | 12/1991 |
| WO | 8912690 A1 | 12/1989 |
| WO | 9200252 A1 | 1/1992 |
| WO | 9428028 | 12/1994 |
| WO | 9518863 A1 | 7/1995 |
| WO | 9521931 A1 | 8/1995 |
| WO | 9617823 A1 | 6/1996 |
| WO | 9625508 A1 | 8/1996 |

(Continued)

OTHER PUBLICATIONS

Perring et al. (1993) Science 259:74-77.*
Michael Ashburner et al., "Temporal Control of Puffing Activity in Polytene Chromosomes", Cold Spring Harbor Symp. Quant. Biol., 1974, 38:655-662.
Tarlochan S. Dhadialla, et al., "New Insecticides with Ecdysteroidal and Juvenile Hormone Activity", Annu. Rev. Entomol, 1998, 43:545-569.
Michael R. Koelle et al., "The Drosophila EcR Gene Encodes an Ecdysone Receptor, a New Member of the Steriod Receptor Superfamily", Cell, 1991, 67: 59-77.
Ravi Kothapalli et al., "Cloning and Developmental Expression of the Ecdysone Receptor Gene From the Spruce Budworm, Choristoneura fumiferana", Developmental Genetics, 1995, 17: 319-30.

(Continued)

Primary Examiner — Michael Pak
(74) Attorney, Agent, or Firm — Sterne, Kessler, Goldstein & Fox, P.L.L.C.

(57) ABSTRACT

The present invention relates to a novel isolated whitefly ecdysone receptor polypeptide. The invention also relates to an isolated nucleic acid encoding the whitefly ecdysone receptor polypeptide, to vectors comprising them and to their uses, in particular in methods for modulating gene expression in an ecdysone receptor-based gene expression modulation system and methods for identifying molecules that modulate whitefly ecdysone receptor activity.

12 Claims, 2 Drawing Sheets

FOREIGN PATENT DOCUMENTS

| WO | 9627673 | | 9/1996 |
|---|---|---|---|
| WO | 9738117 | A1 | 10/1997 |
| WO | 9902683 | A1 | 1/1999 |
| WO | 9936520 | A1 | 7/1999 |
| WO | 9958155 | A1 | 11/1999 |
| WO | WO 01/02436 | | 1/2001 |
| WO | 0170816 | A2 | 9/2001 |
| WO | 0229075 | A2 | 4/2002 |
| WO | 02066612 | A2 | 8/2002 |
| WO | 02066613 | A2 | 8/2002 |
| WO | 02066614 | A2 | 8/2002 |
| WO | 02066615 | A2 | 8/2002 |
| WO | 2005108617 | A2 | 11/2005 |

OTHER PUBLICATIONS

Jean-Francois Mouillet et al., "Cloning of two putative ecdysteroid receptor isoforms from Tenebrio molitor and their developmental expression in the epidermis during metamorphosis", Eur. J. Biochem., 1997, 248: 856-863.

Haruhiko Fujiwara et al., "Cloning of an Ecdysone Receptor Homolog from Manduca sexta and the Developmental Profile of Its mRNA in Wings", Insect Biochem. Molec. Biol., 1995, 25, 845-856.

Alberto Martinez et al., Transcriptional activation of the cloned Heliothis virescens (Lepidopetra) ecdysone receptor (HvEcR) by MuristeroneA, Insect Biochemistry and Molecular Biology, 1999, 29: 915-930.

Markus O. Imhof et al., Cloning of a Chironomus tentans cDNA Encoding a Protein (cEcRH) Homologous to the Drosophila melanogaster Ecdysteroid Receptor (dEcR), Insect Biochem, Molec. Biol., 1993, 23: 115-124.

Luc Swevers et al., "Silkmoth Homolog of the Drosophila Ecdysone Receptor (B1 Isoform): Cloning and Analysis of Expression During Follicular Cell Differentiation", Insect Biochem. Molec. Biol., 1995, 25: 857-866.

Wen-Long Cho et al., "Mosquito Ecdysteroid Receptor: Analysis of the cDNA and Expression During Vitellogenesis", Insect Biochem. Molec. Biol., 1995, 25: 19-27.

Garry N. Hannan et al., "Cloning and Characterization of LcEcR: A Functional Ecdysone Receptor from the Sheep Blowfly Lucilia cuprina", Insect Biochem. Molec. Biol., 1997, 27: 479-488.

Meletis Verras et al., "Cloning and characterization of CcEcR: An ecdysone receptor homolog from the Mediterranean fruit fly Ceratitis capitata", Eur. J. Biochem., 1999, 265: 798-808.

David S. Saleh et al., "Cloning and characterization of an ecdysone receptor cDNA from Locusta migratoria", Molecular and Cellular Endocrinology, 1998, 143: 91-99.

Arthur C.-K. Chung et al., "Cloning of curstacean ecdysteroid receptor and retinoid-X recptor gene homologs and elevation of retinoid-X receptor mRNA by retinoic acid", Molecular and Cellular Endocrinology, 1998, 139: 209-227.

Xiaoping Guo et al., "Isolation of a Functional Ecdysteroid Receptor Homologue from the Ixodid Tick Amblyomma americanum (L.)", Insect Biochem. Molec. Biol., 1997, 27: 945-962.

Ronald M. Evans, "The Steroid and Thyroid Hormone Receptor Superfamily", Science, 1988, 240: 889-895.

Lynn M. Riddiford et al., "Ecdysone Receptors and Their Biological Actions", Vitamins and Hormones, 2000, 60:1-73.

Karen S. Christopherson et al., "Ecdysteroid-dependent regulation of genes in mammalian cells by a Drosophila ecdysone receptor and chimeric transactivators", Proc. Natl. Acad. Sci. U.S.A., 1992, 89: 6314-6318.

David No et al., "Ecdysone-inducible gene expression in mammalian cells and transgenic mice", Proc. Natl. Acad. Sci., 1996, 93: 3346-3351.

Steven T. Suhr et al., High level transactivation by a modified Bombyx ecdysone receptor in mammalian cells without exogenous retinoid X receptor, Proc. Natl. Acad. Sci. U.S.A., 1998, 95: 7999-8004.

Ulrike Heberlein et al., "Characterization of Drosophila Transcription Factors That Activate the Tandem Promoters of the Alcohol Dehydrogenase Gene", Cell, 1985, 41: 965-977.

James M. Wilson et al., "Hepatocyte-directed Gene Transfer in Vivo Leads to Transient Improvement of Hypercholesterolemia Low Density Lipoprotein Receptor-deficient Rabbits", J. Biol. Chem., 1992, 267:963-967.

Michael S. Neuberger et al., "Recombinant antibodies possesing novel effector functions", Nature, 1984, 312: 604-608.

Christophe Antoniewski, et al., "The Ecdysone Response Enhancer of the Fbp1 Gene of Drosophila melanogaster Is a Direct Target for the EcR/USP Nuclear Receptor", Molecular and Cellular Biology, 1994, 14, 4465-4474.

Donald A. Morrison et al., "Isolation of Transformation-Deficient *Streptococcus pneumoniae* Mutants Defective in Control of competence, Using Isertion-Duplicatoin Mutagenesis with the Erythromycin Resistance Determinant of pAMbeta1" , J. Bacteriol. 1984, 159:870.

D. Metzger et al., "The human oestrogen receptor functions in yeast", Nature, 1988, 334:31-36.

Paul J. Godowski et al., "Signal Transduction and Transcriptional Regulation by Glucocorticoid Receptor-LexA Fusion Proeins", Science, 1988, 241: 812-816.

Pier Paolo D'Avino et. al., "The moulting hormone ecdysone is able to recognize target elements composed of direct repeats", Molecular and Cellular Endocrinology, 113: 1-9.

Lucy Cherbas et. al., "Identification of ecdysone response elements by analysis of the Drosophila Eip28/29 gene", Genes & Development, 1991, 5: 120-131.

U.S. Appl. No. 10/490,971, inventor Palli, S., filed Feb. 20, 2002, published as US 2008/0280321 A9.

U.S. Appl. No. 11/852,194, inventor Palli, S., filed Sep. 7, 2007, published as US 2008/0214790 A1.

U.S. Appl. No. 11/837,834, inventor Palli, S., filed Aug. 13, 2007, published as US 2008/0064097 A1.

* cited by examiner

SEQUENCE LISTING

<160> NUMBER OF SEQ ID NOS: 25

<210> SEQ ID NO 1
<211> LENGTH: 1586
<212> TYPE: DNA
<213> ORGANISM: Bamecia argentifoli

<400> SEQUENCE: 1

```
gaattcgcgg ccgctcgcaa acttccgtac ctctcacccc ctcgccagga ccccccgcca      60
accagttcac cgtcatctcc tccaatggat actcatcccc catgtcttcg ggcagctacg     120
acccttatag tcccaccaat ggaagaatag ggaaagaaga gctttcgccg gcgaatagtc     180
tgaacgggta caacgtggat agctgcgatg cgtcgcggaa gaagaaggga ggaacgggtc     240
ggcagcagga ggagctgtgt ctcgtctgcg gggaccgcgc ctccggctac cactacaacg     300
ccctcacctg cgaaggctgc aagggcttct tccgtcggag catcaccaag aatgccgtct     360
accagtgtaa atatggaaat aattgtgaaa ttgacatgta catgaggcga aatgccaag      420
agtgtcgtct caagaagtgt ctcagcgttg catgaggcc agaatgtgta gttcccgaat     480
tccagtgtgc tgtgaagcga aaagagaaaa agcgcaaaa ggacaaagat aaacctaact     540
caacgacgag ttgttctcca gatggaatca acaagagat agatcctcaa aggctggata     600
cagattcgca gctattgtct gtaaatggag ttaaacccat tactccagag caagaagagc     660
tcatccatag gctagtttat tttcaaaatg aatatgaaca tccatcccca gaggatatca     720
aaaggatagt taatgctgca ccagaagaag aaaatgtagc tgaagaaagg tttaggcata     780
ttacagaaat tacaattctc actgtacagt taattgtgga attttctaag cgattacctg     840
gttttgacaa actaattcgt gaagatcaaa tagctttatt aaaggcatgt agtagtgaag     900
taatgatgtt tagaatggca aggaggtatg atgctgaaac agattcgata ttgtttgcaa     960
ctaaccagcc gtatacgaga gaatcataca ctgtagctgg catgggtgat actgtggagg    1020
atctgctccg attttgtcga catatgtgtg ccatgaaagt cgataacgca gaatatgctc    1080
ttctcactgc cattgtaatt ttttcagaac gaccatctct aagtgaaggc tggaaggttg    1140
agaagattca agaaattac atagaagcat taaagcata tgttgaaaat cgaaggaaac    1200
catatgcaac aaccatttt gctaagttac tatctgtttt aactgaacta cgaacattag    1260
ggaatatgaa ttcagaaaca tgcttctcat tgaagctgaa gaatagaaag gtgccatcct    1320
tcctcgagga gatttgggat gttgtttcat aaacagtctt acctcaattc catgttactt    1380
ttcatatttg atttatctca gcaggtggct cagtacttat cctcacatta ctgagctcac    1440
ggtatgctca tacaattata acttgtaata tcatatcggt gatgacaaat ttgttacaat    1500
attctttgtt accttaacac aatgttgatc tcataatgat gtatgaattt ttctgttttt    1560
gcaaaaaaaa aagcggccgc gaattc                                        1586
```

<210> SEQ ID NO 2
<211> LENGTH: 416
<212> TYPE: PRT
<213> ORGANISM: Bamecia argentifoli

<400> SEQUENCE: 2

```
Met Ser Ser Gly Ser Tyr Asp Pro Tyr Ser Pro Thr Asn Gly Arg Ile
1               5                   10                  15

Gly Lys Glu Glu Leu Ser Pro Ala Asn Ser Leu Asn Gly Tyr Asn Val
            20                  25                  30
```

```
Asp Ser Cys Asp Ala Ser Arg Lys Lys Gly Gly Thr Gly Arg Gln
         35                  40                  45

Gln Glu Glu Leu Cys Leu Val Cys Gly Asp Arg Ala Ser Gly Tyr His
     50                  55                  60

Tyr Asn Ala Leu Thr Cys Glu Gly Cys Lys Gly Phe Phe Arg Arg Ser
 65                  70                  75                  80

Ile Thr Lys Asn Ala Val Tyr Gln Cys Lys Tyr Gly Asn Asn Cys Glu
                 85                  90                  95

Ile Asp Met Tyr Met Arg Arg Lys Cys Gln Glu Cys Arg Leu Lys Lys
            100                 105                 110

Cys Leu Ser Val Gly Met Arg Pro Glu Cys Val Val Pro Glu Phe Gln
        115                 120                 125

Cys Ala Val Lys Arg Lys Glu Lys Lys Ala Gln Lys Asp Lys Asp Lys
    130                 135                 140

Pro Asn Ser Thr Thr Ser Cys Ser Pro Asp Gly Ile Lys Gln Glu Ile
145                 150                 155                 160

Asp Pro Gln Arg Leu Asp Thr Asp Ser Gln Leu Leu Ser Val Asn Gly
                165                 170                 175

Val Lys Pro Ile Thr Pro Glu Gln Glu Glu Leu Ile His Arg Leu Val
            180                 185                 190

Tyr Phe Gln Asn Glu Tyr Glu His Pro Ser Pro Glu Asp Ile Lys Arg
        195                 200                 205

Ile Val Asn Ala Ala Pro Glu Glu Asn Val Ala Glu Glu Arg Phe
210                 215                 220

Arg His Ile Thr Glu Ile Thr Ile Leu Thr Val Gln Leu Ile Val Glu
225                 230                 235                 240

Phe Ser Lys Arg Leu Pro Gly Phe Asp Lys Leu Ile Arg Glu Asp Gln
                245                 250                 255

Ile Ala Leu Leu Lys Ala Cys Ser Ser Glu Val Met Met Phe Arg Met
            260                 265                 270

Ala Arg Arg Tyr Asp Ala Glu Thr Asp Ser Ile Leu Phe Ala Thr Asn
        275                 280                 285

Gln Pro Tyr Thr Arg Glu Ser Tyr Thr Val Ala Gly Met Gly Asp Thr
    290                 295                 300

Val Glu Asp Leu Leu Arg Phe Cys Arg His Met Cys Ala Met Lys Val
305                 310                 315                 320

Asp Asn Ala Glu Tyr Ala Leu Leu Thr Ala Ile Val Ile Phe Ser Glu
                325                 330                 335

Arg Pro Ser Leu Ser Glu Gly Trp Lys Val Glu Lys Ile Gln Glu Ile
            340                 345                 350

Tyr Ile Glu Ala Leu Lys Ala Tyr Val Glu Asn Arg Arg Lys Pro Tyr
        355                 360                 365

Ala Thr Thr Ile Phe Ala Lys Leu Leu Ser Val Leu Thr Glu Leu Arg
    370                 375                 380

Thr Leu Gly Asn Met Asn Ser Glu Thr Cys Phe Ser Leu Lys Leu Lys
385                 390                 395                 400

Asn Arg Lys Val Pro Ser Phe Leu Glu Glu Ile Trp Asp Val Val Ser
                405                 410                 415

<210> SEQ ID NO 3
<211> LENGTH: 24
<212> TYPE: DNA
<213> ORGANISM: Artificial Sequence
<220> FEATURE:
<223> OTHER INFORMATION: Degenerate EcR PCR primer
<220> FEATURE:
```

```
<221> NAME/KEY: misc_feature
<222> LOCATION: (3)..(3)
<223> OTHER INFORMATION: n = a or g
<220> FEATURE:
<221> NAME/KEY: misc_feature
<222> LOCATION: (6)..(6)
<223> OTHER INFORMATION: n = a or g
<220> FEATURE:
<221> NAME/KEY: misc_feature
<222> LOCATION: (9)..(9)
<223> OTHER INFORMATION: n = t or c
<220> FEATURE:
<221> NAME/KEY: misc_feature
<222> LOCATION: (12)..(12)
<223> OTHER INFORMATION: n = t, c, a or g
<220> FEATURE:
<221> NAME/KEY: misc_feature
<222> LOCATION: (15)..(15)
<223> OTHER INFORMATION: n = t or c
<220> FEATURE:
<221> NAME/KEY: misc_feature
<222> LOCATION: (18)..(18)
<223> OTHER INFORMATION: n = t, c, a or g
<220> FEATURE:
<221> NAME/KEY: misc_feature
<222> LOCATION: (21)..(21)
<223> OTHER INFORMATION: n = t, c, a or g

<400> SEQUENCE: 3
aanaantgnc tnagngtngg natg                                            24

<210> SEQ ID NO 4
<211> LENGTH: 24
<212> TYPE: DNA
<213> ORGANISM: Artificial Sequence
<220> FEATURE:
<223> OTHER INFORMATION: Degenerate EcR PCR primer
<220> FEATURE:
<221> NAME/KEY: misc_feature
<222> LOCATION: (1)..(1)
<223> OTHER INFORMATION: n = a, g or t
<220> FEATURE:
<221> NAME/KEY: misc_feature
<222> LOCATION: (4)..(4)
<223> OTHER INFORMATION: n = t or c
<220> FEATURE:
<221> NAME/KEY: misc_feature
<222> LOCATION: (7)..(7)
<223> OTHER INFORMATION: n = a or g
<220> FEATURE:
<221> NAME/KEY: misc_feature
<222> LOCATION: (10)..(10)
<223> OTHER INFORMATION: n = t or c
<220> FEATURE:
<221> NAME/KEY: misc_feature
<222> LOCATION: (13)..(13)
<223> OTHER INFORMATION: n = t, a, c or g
<220> FEATURE:
<221> NAME/KEY: misc_feature
<222> LOCATION: (16)..(16)
<223> OTHER INFORMATION: n = a, g or t
<220> FEATURE:
<221> NAME/KEY: misc_feature
<222> LOCATION: (19)..(19)
<223> OTHER INFORMATION: n = t, c, a or g
<220> FEATURE:
<221> NAME/KEY: misc_feature
<222> LOCATION: (22)..(22)
<223> OTHER INFORMATION: n = t or c

<400> SEQUENCE: 4
natntgntcn tcncgnatna gntt                                            24

<210> SEQ ID NO 5
<211> LENGTH: 8
<212> TYPE: PRT
```

```
<213> ORGANISM: Artificial Sequence
<220> FEATURE:
<223> OTHER INFORMATION: Conserved EcR C region

<400> SEQUENCE: 5

Lys Lys Cys Leu Ser Val Gly Met
1               5

<210> SEQ ID NO 6
<211> LENGTH: 8
<212> TYPE: PRT
<213> ORGANISM: Artificial Sequence
<220> FEATURE:
<223> OTHER INFORMATION: Conserved EcR E region

<400> SEQUENCE: 6

Lys Leu Ile Arg Glu Asp Gln Ile
1               5

<210> SEQ ID NO 7
<211> LENGTH: 441
<212> TYPE: DNA
<213> ORGANISM: Bamecia argentifoli

<400> SEQUENCE: 7
aagaagtgtc tcagcgttgg catgaggcca gaatgtgtag ttcccgaatt ccagtgtgct      60
gtgaagcgaa aagagaaaaa agcgcaaaag gacaaagata aacctaactc aacgacgagt     120
tgttctccag atggaatcaa acaagagata gatcctcaaa ggctggatac agattcgcag     180
ctattgtctg taaatggagt taaacccatt actccagagc aagaagagct catccatagg     240
ctagtttatt ttcaaaatga atatgaacat ccatccccag aggatatcaa aaggatagtt     300
aatgctgcac cagaagaaga aaatgtagct gaagaaaggt ttaggcatat tacagaaatt     360
acaattctca ctgtacagtt aattgtggaa ttttctaagc gattacctgg ttttgacaaa     420
ctaattcgtg aagatcaaat a                                               441

<210> SEQ ID NO 8
<211> LENGTH: 90
<212> TYPE: PRT
<213> ORGANISM: herpes simplex virus 7

<400> SEQUENCE: 8

Met Gly Pro Lys Lys Lys Arg Lys Val Ala Pro Pro Thr Asp Val Ser
1               5                   10                  15

Leu Gly Asp Glu Leu His Leu Asp Gly Glu Asp Val Ala Met Ala His
                20                  25                  30

Ala Asp Ala Leu Asp Asp Phe Asp Leu Asp Met Leu Gly Asp Gly Asp
            35                  40                  45

Ser Pro Gly Pro Gly Phe Thr Pro His Asp Ser Ala Pro Tyr Gly Ala
        50                  55                  60

Leu Asp Met Ala Asp Phe Glu Phe Glu Gln Met Phe Thr Asp Ala Leu
65                  70                  75                  80

Gly Ile Asp Glu Tyr Gly Gly Glu Phe Pro
                85                  90

<210> SEQ ID NO 9
<211> LENGTH: 681
<212> TYPE: DNA
<213> ORGANISM: herpes simplex virus 7

<400> SEQUENCE: 9
```

```
atgggcccta aaaagaagaa gcgtaaggtc aaagcgttaa cggccaggct tgaattaatt        60
ccgggcggaa tgaaagcgtt aacgccagg caacaagagg tgtttgatct catccgtgat       120
cacatcagcc agacaggtat gccgccgacg cgtgcggaaa tcgcgcagcg tttggggttc       180
cgttccccaa acgcggctga agaacatctg aaggcgctgg cacgcaaagg cgttattgaa       240
attgtttccg gcgcatcacg cgggattcgt ctgttgcagg aagaggaaga agggttgccg       300
ctggtaggtc gtgtgctgc cggtgaacca cttctggcgc aacagcatat tgaaggtcat       360
tatcaggtcg atccttcctt attcaagccg aatgctgatt tcctgctgcg cgtcagcggg       420
atgtcgatga agatatcgg cattatggat ggtgacttgc tggcagtgca taaaactcag       480
gatgtacgta acggtcaggt cgttgtcgca cgtattgatg acgaagttac cgttaagcgc       540
ctgaaaaaac agggcaataa agtcgaactg ttgccagaaa atagcgagtt taaaccaatt       600
gtcgtagatc ttcgtcagca gagcttcacc attgaagggc tggcggttgg ggttattcgc       660
aacggcgact ggctggaatt c                                                 681

<210> SEQ ID NO 10
<211> LENGTH: 703
<212> TYPE: DNA
<213> ORGANISM: Baculovirus

<400> SEQUENCE: 10
catatgtatc ccgggccagt tgcacaacac tattatcgat ttgcagttcg ggacataaat        60
gtttaaatat atcgatgtct tgtgatgcg cgcgacattt tgtaggtta ttgataaaat       120 gaacggatac gttgcccgac attatcatta aatccttggc gtagaatttg tcgggtccat       180
tgtccgtgtg cgctagcatg cccgtaacgg acctcgtact tttggcttca aaggttttgc       240
gcacagacaa aatgtgccac acttgcagct ctgcatgtgt gcgcgttacc acaaatccca       300
acggcgcagt gtacttgttg tatgcaaata aatctcgata aaggcgcggc gcgcgaatgc       360
agctgatcac gtacgctcct cgtgttccgt tcaaggacgg tgttatcgac ctcagattaa       420
tgtttatcgg ccgactgttt tcgtatccgc tcaccaaacg cgttttttgca ttaacattgt       480 atgtcggcgg atgttctata tctaatttga ataaataaac gataaccgcg ttggttttag       540
agggcataat aaaagaaata ttgttatcgt gttcgccatt agggcagtat aaattgacgt       600
tcatgttgga tattgtttca gttgcaagtt gacactggcg gcgacaagat cgtgaacaac       660
caagtgacta tagaattcac tcgaggctag cataagatct aag                         703

<210> SEQ ID NO 11
<211> LENGTH: 30
<212> TYPE: DNA
<213> ORGANISM: Drosophila melanogaster

<400> SEQUENCE: 11
gagacaaggg ttcaatgcac ttgtccaatg                                         30

<210> SEQ ID NO 12
<211> LENGTH: 3157
<212> TYPE: DNA
<213> ORGANISM: Escherichia coli

<400> SEQUENCE: 12 atgggggggtt ctcatcatca tcatcatcat ggtatggcta gcatgactgg tggacagcaa        60
atgggtcggg atctgtacga cgatgacgat aaggtaccta aggatcagct tggagttgat       120
cccgtcgttt tacaacgtcg tgactgggaa aaccctggcg ttacccaact taatcgcctt       180
```

```
gcagcacatc cccctttcgc cagctggcgt aatagcgaag aggcccgcac cgatcgccct      240
tcccaacagt tgcgcagcct gaatggcgaa tggcgctttg cctggtttcc ggcaccagaa      300
gcggtgccgg aaagctggct ggagtgcgat cttcctgagg ccgatactgt cgtcgtcccc      360
tcaaactggc agatgcacgg ttacgatgcg cccatctaca ccaacgtaac ctatcccatt      420
acggtcaatc cgccgtttgt tcccacggag aatccgacgg gttgttactc gctcacattt      480
aatgttgatg aaagctggct acaggaaggc cagacgcgaa ttattttga tggcgttaac       540 tcggcgtttc atctgtggtg caacgggcgc tgggtcggtt acggccagga cagtcgtttg      600
ccgtctgaat ttgacctgag cgcattttta cgcgccggaa aaaccgcct cgcggtgatg       660 gtgctgcgtt ggagtgacgg cagttatctg gaagatcagg atatgtggcg gatgagcggc      720
attttccgtg acgtctcgtt gctgcataaa ccgactacac aaatcagcga tttccatgtt      780
gccactcgct ttaatgatga tttcagccgc gctgtactgg aggctgaagt tcagatgtgc      840
ggcgagttgc gtgactacct acgggtaaca gtttctttat ggcagggtga aacgcaggtc      900
gccagcggca ccgcgccttt cggcggtgaa attatcgatg agcgtggtgg ttatgccgat      960
cgcgtcacac tacgtctgaa cgtcgaaaac ccgaaactgt ggagcgccga atcccgaat      1020 ctctatcgtg cggtggttga actgcacacc gccgacggca cgctgattga agcagaagcc      1080
tgcgatgtcg gtttccgcga ggtgcggatt gaaaatggtc tgctgctgct gaacggcaag      1140
ccgttgctga ttcgaggcgt taaccgtcac gagcatcatc ctctgcatgg tcaggtcatg      1200
gatgagcaga cgatggtgca ggatatcctg ctgatgaagc agaacaactt taacgccgtg      1260
cgctgttcgc attatccgaa ccatccgctg tggtacacgc tgtgcgaccg ctacggcctg      1320
tatgtggtgg atgaagccaa tattgaaacc cacggcatgg tgccaatgaa tcgtctgacc      1380
gatgatccgc gctggctacc ggcgatgagc gaacgcgtaa cgcgaatggt gcagcgcgat      1440
cgtaatcacc cgagtgtgat catctggtcg ctggggaatg aatcaggcca cggcgctaat      1500
cacgacgcgc tgtatcgctg gatcaaatct gtcgatcctt cccgcccggt gcagtatgaa      1560
ggcggcggag ccgacaccac ggccaccgat attatttgcc cgatgtacgc gcgcgtggat      1620
gaagaccagc ccttcccggc tgtgccgaaa tggtccatca aaaaatggct ttcgctacct      1680
ggagagacgc gcccgctgat cctttgcgaa tacgcccacg cgatgggtaa cagtcttggc      1740
ggtttcgcta atactggca ggcgtttcgt cagtatcccc gtttacaggg cggcttcgtc       1800
tgggactggg tggatcagtc gctgattaaa tatgatgaaa acggcaaccc gtggtcggct      1860 tacgcggtg attttggcga tacgccgaac gatcgccagt tctgtatgaa cggtctggtc      1920
tttgccgacc gcacgccgca tccagcgctg acggaagcaa acaccagca gcagttttc       1980 cagttccgtt tatccgggca aaccatcgaa gtgaccagcg aatacctgtt ccgtcatagc      2040
gataacgagc tcctgcactg gatggtggcg ctggatggta agccgctggc aagcggtgaa      2100
gtgcctctgg atgtcgctcc acaaggtaaa cagttgattg aactgcctga actaccgcag      2160
ccggagagcg ccgggcaact ctggctcaca gtacgcgtag tgcaaccgaa cgcgaccgca      2220
tggtcagaag ccgggcacat cagcgcctgg cagcagtggc gtctggcgga aaacctcagt      2280
gtgacgctcc ccgccgcgtc ccacgccatc ccgcatctga ccaccagcga atggattttt      2340
tgcatcgagc tgggtaataa gcgttggcaa tttaaccgcc agtcaggctt tctttcacag      2400
atgtggattg gcgataaaaa acaactgctg acgccgctgc gcgatcagtt cacccgtgca      2460
ccgctggata cgacattggg cgtaagtgaa gcgacccgca ttgaccctaa cgcctgggtc      2520
gaacgctgga aggcggcggg ccattaccag gccgaagcag cgttgttgca gtgcacggca      2580
```

```
gatacacttg ctgatgcggt gctgattacg accgctcacg cgtggcagca tcagggaaa     2640 accttattta tcagccggaa aacctaccgg attgatggta gtggtcaaat ggcgattacc    2700
gttgatgttg aagtggcgag cgatacaccg catccggcgc ggattggcct gaactgccag    2760
ctggcgcagg tagcagagcg ggtaaactgg ctcggattag ggccgcaaga aaactatccc    2820
gaccgcctta ctgccgcctg ttttgaccgc tgggatctgc cattgtcaga catgtatacc    2880
ccgtacgtct tcccgagcga aaacggtctg cgctgcggga cgcgcgaatt gaattatggc    2940
ccacaccagt ggcgcggcga cttccagttc aacatcagcc gctacagtca acagcaactg    3000
atggaaaccc gccatcgcca tctgctgcac gcggaagaag gcacatggct gaatatcgac    3060
ggtttccata tggggattgg tggcgacgac tcctggagcc cgtcagtatc ggcggaatta    3120
cagctgagcg ccggtcgcta ccattaccag ttggtct                              3157
```

<210> SEQ ID NO 13
<211> LENGTH: 147
<212> TYPE: PRT
<213> ORGANISM: Saccharomyces cerevisiae

<400> SEQUENCE: 13

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser
145
```

<210> SEQ ID NO 14
<211> LENGTH: 441
<212> TYPE: DNA
<213> ORGANISM: Saccharomyces cerevisiae

<400> SEQUENCE: 14

```
atgaagctac tgtcttctat cgaacaagca tgcgatattt gccgacttaa aaagctcaag     60
tgctccaaag aaaaaccgaa gtgcgccaag tgtctgaaga caactgggga gtgtcgctac    120
tctcccaaaa ccaaaaggtc tccgctgact agggcacatc tgacagaagt ggaatcaagg    180
ctagaaagac tggaacagct atttctactg attttttcctc gagaagacct tgacatgatt    240
ttgaaaatgg attcttttaca ggatataaaa gcattgttaa caggattatt tgtacaagat    300
aatgtgaata agatgccgt cacagataga ttggcttcag tggagactga atgcctcta     360 acattgagac agcatagaat aagtgcgaca tcatcatcgg aagagagtag taacaaaggt    420
```

```
caaagacagt tgactgtatc g                                              441
```

<210> SEQ ID NO 15
<211> LENGTH: 750
<212> TYPE: DNA
<213> ORGANISM: Cytomegalovirus

<400> SEQUENCE: 15

```
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg accccgccc attgacgtca ataatgacgt atgttcccat     300
agtaacgcca tagggacttt ccattgacg tcaatgggtg gagtatttac ggtaaactgc     360
ccacttggca gtacatcaag tgtatcatat gccaagtccg ccccctattg acgtcaatga    420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg ggatttcca agtctccacc ccattgacgt     600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc                                     750
```

<210> SEQ ID NO 16
<211> LENGTH: 798
<212> TYPE: DNA
<213> ORGANISM: Choristoneura fumiferana

<400> SEQUENCE: 16

```
tcggtgcagg taagcgatga gctgtcaatc gagcgcctaa cggagatgga gtctttggtg     60
gcagatccca gcgaggagtt ccagttcctc cgcgtggggc ctgacagcaa cgtgcctcca    120
cgttaccgcg cgcccgtctc ctccctctgc caaataggac acaagcaaat agcggcgttg    180
gtggtatggg cgcgcgacat ccctcatttc gggcagctgg agctggacga tcaagtggta    240
ctcatcaagg cctcctggaa tgagctgcta ctcttcgcca tcgcctggcg ctctatggag    300
tatttggaag atgagaggga gaacggggac ggaacgcgga gcaccactca gccacaactg    360
atgtgtctca tgcctggcat gacgttgcac cgcaactcgg cgcagcaggc gggcgtgggc    420
gccatcttcg accgcgtgct gtccgagctc agtctgaaga tgcgcacctt gcgcatggac    480
caggccgagt acgtcgcgct caaagccatc gtgctgctca accctgatgt gaaaggactg    540
aagaatcggc aagaagttga cgttttgcga gaaaaatgt tctcttgcct ggacgactac     600
tgccggcggt cgcgaagcaa cgaggaaggc cggtttgcgt ccttgctgct gcggctgcca    660
gctctccgct ccatctcgct caagagcttc gaacacctct acttcttcca cctcgtggcc    720
gaaggctcca tcagcggata catacgagag gcgctccgaa accacgcgcc tccgatcgac    780
gtcaatgcca tgatgtaa                                                  798
```

<210> SEQ ID NO 17
<211> LENGTH: 799
<212> TYPE: DNA
<213> ORGANISM: Drosophila melanogaster

<400> SEQUENCE: 17

```
catagaggcc gagcagcgag cggagaccca atgcggcgat cgtgcactga cgttcctgcg    60
cgttggtccc tattccacag tccagccgga ctacaaggt gccgtgtcgg ccctgtgcca    120
agtggtcaac aaacagctct tccagatggt cgaatacgcg cgcatgatgc cgcactttgc   180
ccaggtgccg ctggacgacc aggtgattct gctgaaagcc gcttggatcg agctgctcat   240
tgcgaacgtg gcctggtgca gcatcgtttc gctggatgac ggcggtgccg gcggcggggg   300
cggtggacta ggccacgatg gctcctttga gcgacgatca ccgggccttc agccccagca   360
gctgttcctc aaccagagct tctcgtacca tcgcaacagt gcgatcaaag ccggtgtgtc   420
agccatcttc gaccgcatat tgtcggagct gagtgtaaag atgaagcggc tgaatctcga   480
ccgacgcgag ctgtcctgct tgaaggccat catactgtac aacccggaca tacgcgggat   540
caagagccgg gcgagatcg agatgtgccg cgagaaggtg tacgcttgcc tggacgagca   600
ctgccgcctg gaacatccgg gcgacgatgg acgctttgcg caactgctgc tgcgtctgcc   660
cgcttttgcga tcgatcagcc tgaagtgcca ggatcacctg ttcctcttcc gcattaccag   720
cgaccggccg ctggaggagc tctttctcga gcagctggag gcgccgccgc cacccggcct   780
ggcgatgaaa ctggagtag                                                799
```

<210> SEQ ID NO 18
<211> LENGTH: 635
<212> TYPE: DNA
<213> ORGANISM: Locusta migratoria

<400> SEQUENCE: 18

```
tgcatacaga catgcctgtt gaacgcatac ttgaagctga aaaacgagtg gagtgcaaag    60
cagaaaacca gtggaatat gagctggtgg agtgggctaa acacatcccg cacttcacat    120
ccctacctct ggaggaccag gttctcctcc tcagagcagg ttggaatgaa ctgctaattg   180
cagcattttc acatcgatct gtagatgtta aagatggcat agtacttgcc actggtctca   240
cagtgcatcg aaattctgcc catcaagctg gagtcggcac aatatttgac agagttttga   300
cagaactggt agcaaagatg agagaaatga aaatgcataa aactgaactt ggctgcttgc   360
gatctgttat tcttttcaat ccagaggtga ggggtttgaa atccgcccag gaagttgaac   420
ttctacgtga aaagtatat gccgcttttgg aagaatatac tagaacaaca catcccgatg   480
aaccaggaag atttgcaaaa cttttgcttc gtctgccttc tttacgttcc ataggcctta   540
agtgttttgga gcatttgttt ttcttctcgcc ttattggaga tgttccaatt gatacgttcc   600
tgatggagat gcttgaatca ccttctgatt cataa                             635
```

<210> SEQ ID NO 19
<211> LENGTH: 714
<212> TYPE: DNA
<213> ORGANISM: Mus musculus

<400> SEQUENCE: 19

```
gccaacgagg acatgcctgt agagaagatt ctggaagccg agcttgctgt cgagcccaag    60
actgagacat acgtggaggc aaacatgggg ctgaacccca gctcaccaaa tgaccctgtt   120
accaacatct gtcaagcagc agacaagcag ctcttcactc ttgtggagtg ggccaagagg   180
atcccacact tttctgagct gccctagac gaccaggtca tcctgctacg ggcaggctgg   240
aacgagctgc tgatcgcctc cttctcccac cgctccatag ctgtgaaaga tgggattctc   300
ctggccaccg gcctgcacgt acaccggaac agcgctcaca gtgctggggt gggcgccatc   360
tttgacaggg tgctaacaga gctggtgtct aagatgcgtg acatgcagat ggacaagacg   420
```

```
gagctgggct gcctgcgagc cattgtcctg ttcaaccctg actctaaggg gctctcaaac    480
cctgctgagg tggaggcgtt gagggagaag gtgtatgcgt cactagaagc gtactgcaaa    540
cacaagtacc ctgagcagcc gggcaggttt gccaagctgc tgctccgcct gcctgcactg    600
cgttccatcg ggctcaagtg cctggagcac ctgttcttct tcaagctcat cggggacacg    660
cccatcgaca ccttcctcat ggagatgctg gaggcaccac atcaagccac ctag          714
```

<210> SEQ ID NO 20
<211> LENGTH: 711
<212> TYPE: DNA
<213> ORGANISM: Artificial Sequence
<220> FEATURE:
<223> OTHER INFORMATION: Chimeric MmRXRalpha/LmUSP-EF

<400> SEQUENCE: 20

```
gccaacgagg acatgcctgt agagaagatt ctggaagccg agcttgctgt cgagcccaag     60
actgagacat acgtggaggc aaacatgggg ctgaacccca gctcaccaaa tgaccctgtt    120
accaacatct gtcaagcagc agacaagcag ctcttcactc ttgtggagtg ggccaagagg    180
atcccacact tttctgagct gccccctagac gaccaggtca tcctgctacg ggcaggctgg    240
aacgagctgc tgatcgcctc cttctcccac cgctccatag ctgtgaaaga tgggattctc    300
ctggccaccg gctgcacgt acaccggaac agcgctcaca gtgctggggt gggcgccatc     360
tttgacaggg tgctaacaga gctggtgtct aagatgcgtg acatgcagat ggacaagact    420
gaacttggct gcttgcgatc tgttattctt ttcaatccag aggtgagggg tttgaaatcc    480
gcccaggaag ttgaacttct acgtgaaaaa gtatatgccg ctttggaaga atatactaga    540
acaacacatc ccgatgaacc aggaagattt gcaaaacttt tgcttcgtct gccttcttta    600
cgttccatag gccttaagtg tttggagcat tgttttttct ttcgccttat tggagatgtt    660
ccaattgata cgttcctgat ggagatgctt gaatcacctt ctgattcata a             711
```

<210> SEQ ID NO 21
<211> LENGTH: 687
<212> TYPE: DNA
<213> ORGANISM: Amblyomma americanum

<400> SEQUENCE: 21

```
cctcctgaga tgcctctgga gcgcatactg gaggcagagc tgcgggttga gtcacagacg     60
gggaccctct cggaaagcgc acagcagcag gatccagtga gcagcatctg ccaagctgca    120
gaccgacagc tgcaccagct agttcaatgg gccaagcaca ttccacattt tgaagagctt    180
ccccttgagg accgcatggt gttgctcaag gctggctgga acgagctgct cattgctgct    240
ttctcccacc gttctgttga cgtgcgtgat ggcattgtgc tcgctacagg tcttgtggtg    300
cagcggcata gtgctcatgg ggctggcgtt ggggccatat ttgatagggt tctcactgaa    360
ctggtagcaa agatgcgtga gatgaagatg accgcactg agcttggatg cctgcttgct    420
gtggtacttt ttaatcctga ggccaagggg ctgcggacct gcccaagtgg aggccctgag    480
ggagaaagtg tatctgcctt ggaagagcac tgccggcagc agtacccaga ccagcctggg    540
cgctttgcca agctgctgct gcggttgcca gctctgcgca gtattggcct caagtgcctc    600
gaacatctct ttttcttcaa gctcatcggg gacacgccca tcgacaactt tcttcttttcc    660 atgctggagg cccccctctga cccctaa                                        687
```

<210> SEQ ID NO 22
<211> LENGTH: 693
<212> TYPE: DNA

<213> ORGANISM: Amblyomma americanum

<400> SEQUENCE: 22

```
tctccggaca tgccactcga acgcattctc gaagccgaga tgcgcgtcga gcagccggca      60
ccgtccgttt tggcgcagac ggccgcatcg ggccgcgacc ccgtcaacag catgtgccag     120
gctgccccgc cacttcacga gctcgtacag tgggcccggc gaattccgca cttcgaagag     180
cttcccatcg aggatcgcac cgcgctgctc aaagccggct ggaacgaact gcttattgcc     240
gccttttcgc accgttctgt ggcggtgcgc gacggcatcg ttctggccac cgggctggtg     300
gtgcagcggc acagcgcaca cggcgcaggc gttggcgaca tcttcgaccg cgtactagcc     360
gagctggtgg ccaagatgcg cgacatgaag atggacaaaa cggagctcgg ctgcctgcgc     420
gccgtggtgc tcttcaatcc agacgccaag ggtctccgaa acgccaccag agtagaggcg     480
ctccgcgaga aggtgtatgc ggcgctggag gagcactgcc gtcggcacca cccggaccaa     540
ccgggtcgct tcggcaagct gctgctgcgg ctgcctgcct tgcgcagcat cgggctcaaa     600
tgcctcgagc atctgttctt cttcaagctc atcggagaca ctcccataga cagcttcctg     660
ctcaacatgc tggaggcacc ggcagacccc tag                                  693
```

<210> SEQ ID NO 23
<211> LENGTH: 17
<212> TYPE: DNA
<213> ORGANISM: Saccharomyces cerevisiae

<400> SEQUENCE: 23

```
cggagtactg tcctccg                                                     17
```

<210> SEQ ID NO 24
<211> LENGTH: 30
<212> TYPE: DNA
<213> ORGANISM: Artificial Sequence
<220> FEATURE:
<223> OTHER INFORMATION: Synthetic TATAA

<400> SEQUENCE: 24

```
tagagggtat ataatggatc cccgggtacc                                       30
```

<210> SEQ ID NO 25
<211> LENGTH: 1705
<212> TYPE: DNA
<213> ORGANISM: Photinus pyralis

<400> SEQUENCE: 25

```
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatat cgaggtgaac atcacgtacg cggaatactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgaacatt     360
tcgcagccta ccgtagtgtt tgtttccaaa aaggggttgc aaaaaatttt gaacgtgcaa     420
aaaaaattac caataatcca gaaaattatt atcatggatt ctaaaacgga ttaccaggga     480
tttcagtcga tgtacacgtt cgtcacatct catctacctc ccggttttaa tgaatacgat     540
tttgtaccag agtcctttga tcgtgacaaa acaattgcac tgataatgaa ttcctctgga     600
tctactgggt tacctaaggg tgtggccctt ccgcatagaa ctgcctgcgt cagattctcg     660
```

```
catgccagag atcctatttt tggcaatcaa atcattccgg atactgcgat tttaagtgtt      720
gttccattcc atcacggttt tggaatgttt actacactcg gatatttgat atgtggattt      780
cgagtcgtct taatgtatag atttgaagaa gagctgtttt tacgatccct tcaggattac      840
aaaattcaaa gtgcgttgct agtaccaacc ctattttcat tcttcgccaa aagcactctg      900
attgacaaat acgatttatc taatttacac gaaattgctt ctgggggcgc acctctttcg      960
aaagaagtcg gggaagcggt tgcaaaacgc ttccatcttc cagggatacg acaaggatat     1020
gggctcactg agactacatc agctattctg attacacccg aggggatga taaaccgggc     1080 gcggtcggta aagttgttcc attttttgaa gcgaaggttg tggatctgga taccgggaaa     1140
acgctgggcg ttaatcagag aggcgaatta tgtgtcagag gacctatgat tatgtccggt     1200
tatgtaaaca atccggaagc gaccaacgcc ttgattgaca aggatggatg gctacattct     1260
ggagacatag cttactggga cgaagacgaa cacttcttca tagttgaccg cttgaagtct     1320
ttaattaaat acaaaggata tcaggtggcc cccgctgaat tggaatcgat attgttacaa     1380 cacccccaaca tcttcgacgc gggcgtggca ggtcttcccg acgatgacgc cggtgaactt    1440
cccgccgccg ttgttgtttt ggagcacgga aagacgatga cggaaaaaga gatcgtggat    1500
tacgtcgcca gtcaagtaac aaccgcgaaa aagttgcgcg gaggagttgt gtttgtggac    1560
gaagtaccga aaggtcttac cggaaaactc gacgcaagaa aaatcagaga gatcctcata    1620
aaggccaaga agggcggaaa gtccaaattg taaaatgtaa ctgtattcag cgatgacgaa    1680
attcttagct attgtaatac tctag                                          1705
```

WHITEFLY ECDYSONE RECEPTOR NUCLEIC ACIDS, POLYPEPTIDES, AND USES THEREOF

This application is the U.S. national phase of International Application No. PCT/US02/005234, filed Feb. 20, 2002, which claims the benefit of U.S. Provisional Application No. 60/325,534, filed Sep. 26, 2001.

FIELD OF THE INVENTION

This invention relates to the field of biotechnology. Specifically, this invention relates to isolated nucleic acids, vectors comprising them, and polypeptides encoded by them, and to their use in the field of gene expression and insecticide discovery. More specifically, this invention relates to a novel nucleic acid encoding an ecdysone receptor polypeptide from the homopteran whitefly (*Bamecia argentifoli*, "BaEcR") and its use in methods of modulating the expression of a gene within a host cell using BaEcR, and in methods of identifying molecules that modulate the activity of the BaEcR

BACKGROUND OF THE INVENTION

Various publications are cited herein, the disclosures of which are incorporated by reference in their entireties. However, the citation of any reference herein should not be construed as an admission that such reference is available as "Prior Art" to the instant application.

Cultivated agriculture has greatly increased efficiency of food production in the world. However, various insect pests have found it advantageous to seek out and exploit cultivated sources of food to their own advantage. These insect pests typically develop by a temporal sequence of events which are characteristic of their order. Many insects initially develop in a caterpillar or maggot-like larval form. Thereafter, they undergo a significant metamorphosis from which an adult emerges having characteristic anatomical features. Anatomic similarity is a reflection of developmental, physiological and biochemical similarities shared by these creatures. In particular, the principles of the insect ecdysteroid-hormone receptors and development, as described by Ashburner et al. (Cold Spring Harbor Symp. Quant. Biol. 38:655-662, 1974), likely would be shared by many different types of insects.

To prevent or reduce the destruction of cultivated crops by insects, organic molecules with pesticidal properties are used commonly in attempts to eliminate or reduce the insect populations. However, the ecological side effects of these pesticides, due in part to their broad activity and lack of specificity, and in part, to the fact that some of these pesticides are not easily biodegradable, significantly affect populations of both insect and other species of animals. Some of these organisms may be advantageous from an ecological or other perspective. Furthermore, as the insect populations evolve in directions to minimize the effects of the applied pesticides, the amounts of pesticides applied are often elevated so high as to cause significant effects on other animals, including humans, which are affected directly or indirectly by the application of the pesticides. Thus, an important need exists for both highly specific pesticides or highly active pesticides which have biological effects only on the species of animals targeted by the pesticides, and are biodegradable. Novel insect hormones which, like the ecdysteroids, act by complexing with insect members of the steroid receptor superfamily to control insect development, are likely candidates for pesticides with these desirable properties.

Growth, molting, and development in insects are regulated by the ecdysone steroid hormone (molting hormone) and the juvenile hormones (Dhadialla, et al., 1998, Annu. Rev. Entomol. 43: 545-569). The molecular target for ecdysone in insects consists of at least ecdysone receptor (EcR) and ultraspiracle protein (USP). EcR is a member of the nuclear steroid receptor super family that is characterized by signature DNA and ligand binding domains, and an activation domain (Koelle et al. 1991, Cell, 67:59-77). EcR receptors are responsive to a number of steroidal compounds such as ponasterone A and muristerone A. Recently, non-steroidal compounds with ecdysteroid agonist activity have been described, including the commercially available insecticides tebufenozide and methoxyfenozide (see International Patent Application No. PCT/EP96/00686 and U.S. Pat. No. 5,530,028). Both analogs have exceptional safety profiles to other organisms.

Polynucleotides encoding ecdysone receptors have been cloned from a variety of insect species, including Dipterans (see U.S. Pat. Nos. 5,514,578 and 6,245,531 B1), Lepidopterans, Orthopterans, Hemipterans, and one Homopteran Aphid, all from the class Arthropod. In particular, EcRs have been cloned from spruce budworm *Choristoneura furniferana* EcR ("CfEcR"; Kothapalli et al., 1995 Dev Genet. 17: 319-30), a yellow meal worm *Tenebrio molitor* EcR ("TmEcR"; Mouillet et al., 1997, Eur. J. biochem. 248: 856-863), a tobacco hormworm *Manduca sexta* EcR ("MsEcR"; Fujiwara et al., 1995, Insect Biochem. Molec. Biol. 25, 845-856), a tobacco budworm *Heliotliies virescens* EcR ("HvEcR"; Martinez et al., 1999, *Insect Biochem Mol. Biol.* 29: 915-30), a golmidge *Chironomus tentans* EcR ("CtEcR"; Imhof et al., 1993, Insect Biochem. Molec. Biol. 23, 115-124), a silkworm *Bombyx mori* EcR ("BmEcR"; Swevers et al., 1995, Insect Biochem. Molec. Biol. 25, 857-866), a squinting bush brown *Bicyclus anynana* EcR ("BanEcR"), a buckeye *Junonia coenia* EcR ("JcEcR"), a fruit fly *Drosophila melanogaster* EcR ("DmEcR"; Koelle et al., 1991, Cell 67, 59-77), a yellow fever mosquito *Aedes aegypti* EcR ("AaEcR"; Cho et al., 1995, Insect Biochem Molec. Biol. 25, 19-27), a blowfly *Lucilia capitata* ("LcEcR"), a sheep blowfly *Lucilia cuprina* EcR ("LucEcR"; Hannan and Hill, 1997, Insect Biochem. Molec. Biol. 27, 479-488), a blowfly *Calliphora vicinia* EcR ("CvEcR"), a Mediterranean fruit fly *Ceratitis capitata* EcR ("CcEcR"; Verras et al., 1999, *Eur J Biochem.* 265: 798-808), a locust *Locusta migratoria* EcR ("LmEcR"; Saleh et al., 1998, *Mol Cell Endocrinol.* 143: 91-9), an aphid *Myzus persicae* EcR ("MpEcR"; International Patent Application Publication WO99/36520), a fiddler crab *Celuca pugilator* EcR ("CpEcR"; Chung et al., 1998, *Mol Cell Endocrinol* 139: 209-27), and an ixodid tick *Amblyomma americanum* EcR ("AmaEcR"; Guo et al., 1997, Insect Biochem. Molec. Biol. 27: 945-962). The nucleotide and/or amino acid sequences of these ecdysone receptors have been determined and are publicly available.

The ecdysone receptor complex typically includes proteins that are members of the nuclear receptor superfamily wherein all members are generally characterized by the presence of an amino-terminal transactivation domain, a DNA binding domain ("DBD"), and a ligand binding domain ("LBD") separated from the DBD by a hinge region. As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat.

No. 4,981,784 and Evans, *Science* 240:889-895 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins. The EcR receptor, like a subset of the steroid receptor family, also possesses less well-defined regions responsible for heterodimerization properties. Because the domains of nuclear receptors are modular in nature, the LBD, DBD, and transactivation domains may be interchanged.

Gene switch systems are known that incorporate components from the ecdysone receptor complex. However, in these known systems, whenever EcR is used it is associated with native or modified DNA binding domains and transactivation domains on the same molecule. USP or RXR are typically used as silent partners. Applicants have previously shown that when DNA binding domains and transactivation domains are on the same molecule the background activity in the absence of ligand is high and that such activity is dramatically reduced when DNA binding domains and transactivation domains are on different molecules, that is, on each of two partners of a heterodimeric or homodimeric complex (see PCT/US01/09050).

The insect ecdysone receptor (EcR) heterodimerizes with Ultraspiracle (USP), the insect homologue of the mammalian RXR, and binds ecdysteroids and ecdysone receptor response elements and activates transcription of ecdysone responsive genes (Riddiford et al. 2000, Vitam Horm, 60: 1-73). The EcR/USP/ligand complexes play important roles during insect development and reproduction. The EcR is a member of the steroid hormone receptor superfamily and has five modular domains, A/B (transactivation), C (DNA binding, heterodimerization), D (Hinge, heterodimerization), E (ligand binding, heterodimerization and transactivation and in some cases, F (transactivation), domains. Some of these domains such as A/B, C and E retain their function when they are fused to other proteins.

Recently, ecdysone receptor based gene expression systems have been developed. Tightly regulated inducible gene expression systems or "gene switches" are useful for various applications such as gene therapy, large scale production of proteins in cells, cell based high throughput screening assays, functional genomics and regulation of traits in transgenic plants and animals. U.S. Pat. No. 6,265,173 B1 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins.

The first version of an EcR-based gene switch used *Drosophila melanogaster* EcR (DmEcR) and *Mus musculus* RXR (MmRXR) and showed that these receptors in the presence of steroid, ponasterone A, transactivate reporter genes in mammalian cell lines and transgenic mice (Christopherson et al. 1992, PNAS 89:6314-6318; No et al. 1996, PNAS 93:3346-3351). Later, Suhr et al. (1998, Proc. Natl. Acad. Sci. U.S.A. 95: 7999-8004) showed that non-steroidal ecdysone agonist, tebufenozide, induced high level of transactivation of reporter genes in mammalian cells through *Bombyx mori* EcR (BmEcR) in the absence of exogenous heterodimer partner.

International Patent Applications Nos. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefore, and optionally in the presence of a receptor capable of acting as a silent partner, binds to the ecdysone response element to induce gene expression. The ecdysone receptor of choice was isolated from *Drosophila melanogaster*. Typically, such systems require the presence of the silent partner, preferably retinoid X receptor (RXR), in order to provide optimum activation. In mammalian cells, insect ecdysone receptor (EcR) heterodimerizes with retinoid X receptor (RXR) and regulates expression of target genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

Unfortunately, these USP-based systems are constitutive in animal cells and therefore, are not effective for regulating reporter gene expression. Drawbacks of the above described EcR-based gene regulation systems include a considerable background activity in the absence of ligands and non-applicability of these systems for use in both plants and animals (see U.S. Pat. No. 5,880,333).

Recently, an improved ecdysone receptor-based inducible gene expression system has been developed in which the transactivation and DNA binding domains are separated from each other by placing them on two different proteins results in greatly reduced background activity in the absence of a ligand and significantly increased activity over background in the presence of a ligand (pending application PCT/US01/09050, incorporated herein in its entirety by reference). This two-hybrid system is a significantly improved inducible gene expression modulation system compared to the two systems disclosed in applications PCT/US97/05330 and PCT/US98/14215. The two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). Briefly, the two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, the interaction of the first polypeptide with the second polypeptide effectively tethers the DNA binding domain to the transactivation domain. Since the DNA binding and transactivation domains reside on two different molecules, the background activity in the absence of ligand is greatly reduced.

A two-hybrid system also provides improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provide higher activity at a lower concentration. In addition, since transactivation based on EcR gene switches is often cell-line dependent, it is easier to tailor switching systems to obtain maximum transactivation capability for each application. Furthermore, the two-hybrid system avoids some side effects due to overexpression of RXR that often occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell resulting in reduced side effects.

Applicants have now obtained and determined the full-length coding sequence of an additional homopteran EcR polynucleotide from whitefly for use in methods of modulating gene expression in a host cell and methods of identifying molecules that modulate activity of whitefly EcR. As described herein, Applicants' invention provides novel whitefly ecdysone receptor polypeptides and novel polynucleotides encoding these polypeptides that are useful as components of gene expression systems for highly specific regulation of recombinant proteins in host cells or in methods for identifying new molecules which may act as agonists or antagonists of a homopteran insect ecdysone receptor.

DETAILED DESCRIPTION OF THE INVENTION

Figure 1:
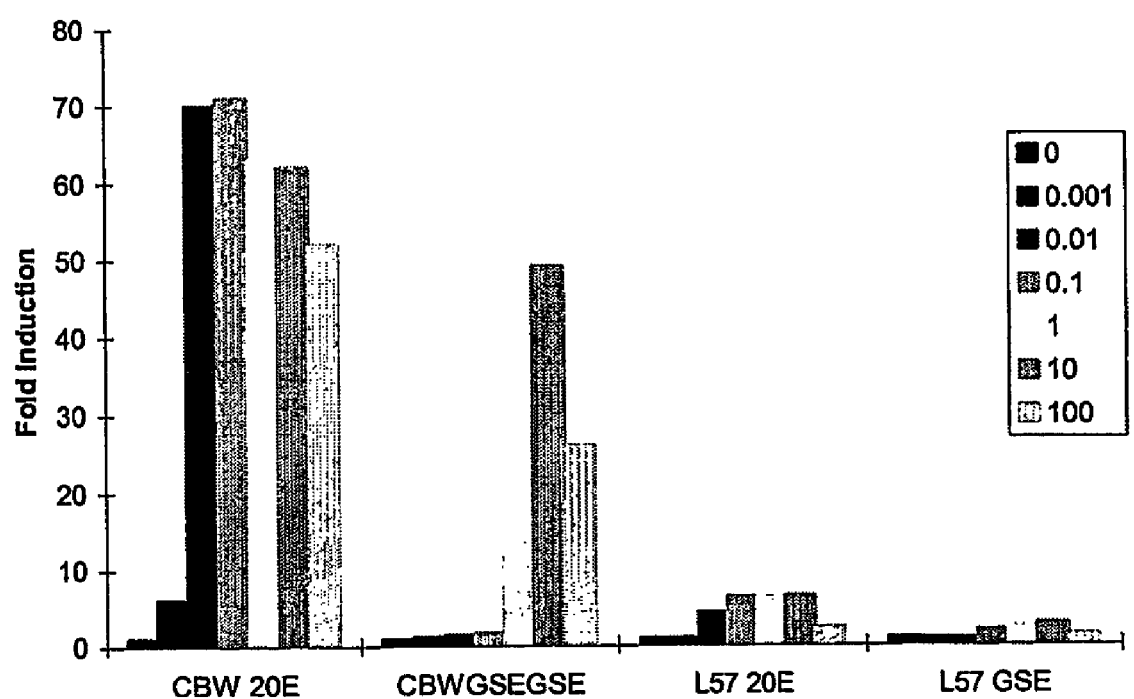
FIG. 1: Transactivation of reporter genes through VP16/BaEcR-CDE construct transfected into L57 cells or CBW cells along with 5XEcRELacZ and pFREcRE by 20E or GS™-E. The numbers on top of the bars indicate fold increase over DMSO levels.

The present invention advantageously provides an isolated polynucleotide encoding a novel whitefly ecdysone receptor polypeptide. The polynucleotides and polypeptides of the present invention are useful in methods to regulate gene expression of a polypeptide of interest in a host cell and in identifying new molecules that modulate activity of a whitefly EcR.

The various aspects of the invention will be set forth in greater detail in the following sections, directed to the nucleic acids, polypeptides, vectors, antibodies, compositions, and methods of use of the invention. This organization into various sections is intended to facilitate understanding of the invention, and is in no way intended to be limiting thereof.

Definitions

The following defined terms are used throughout the present specification, and should be helpful in understanding the scope and practice of the present invention.

In a specific embodiment, the term "about" or "approximately" means within 20%, preferably within 10%, more preferably within 5%, and even more preferably within 1% of a given value or range.

The term "substantially free" means that a composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The term "isolated" for the purposes of the present invention designates a biological material (nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated". The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, preferably 2 or 3 and preferably 4 or 5 orders of magnitude.

As used herein, the term "substantially pure" describes a polypeptide or other material which has been separated from its native contaminants. Typically, a monomeric polypeptide is substantially pure when at least about 60 to 75% of a sample exhibits a single polypeptide backbone. Minor variants or chemical modifications typically share the same polypeptide sequence. Usually a substantially pure polypeptide will comprise over about 85 to 90% of a polypeptide sample, and preferably will be over about 99% pure. Normally, purity is measured on a polyacrylamide gel, with homogeneity determined by staining. Alternatively, for certain purposes high resolution will be necessary and HPLC or a similar means for purification will be used. For most purposes, a simple chromatography column or polyacrylamide gel will be used to determine purity.

The term "substantially free of naturally-associated host cell components" describes a polypeptide or other material which is separated from the native contaminants which accompany it in its natural host cell state. Thus, a polypeptide which is chemically synthesized or synthesized in a cellular system different from the host cell from which it naturally originates will be free from its naturally-associated host cell components.

The terms "nucleic acid" or "polynucleotide" are used interchangeably herein to refer to a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes but is not limited to cDNA, genomic DNA, plasmids DNA, synthetic DNA, and semi-synthetic DNA. DNA may be linear, circular, or supercoiled.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological mranipulation.

The term "fragment" will be understood to mean a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6-1100 consecutive nucleotides of a nucleic acid according to the invention.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous" DNA refers to DNA not naturally located in the cell, or in a chromosomal site of the cell. Preferably, the heterologous DNA includes a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g. 40% formamide, with 5× or 6×SCC. High stringency hybridization conditions correspond to the highest $T_m$, e.g., 50% formamide, 5× or 6×SCC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as disclosed or used herein as well as those substantially similar nucleic acid sequences.

In a specific embodiment of the invention, polynucleotides are detected by employing hybridization conditions comprising a hybridization step at $T_m$ of 55° C., and utilizing conditions as set forth above. In a preferred embodiment, the $T_m$ is 60° C.; in a more preferred embodiment, the $T_m$ is 63° C.; in an even more preferred embodiment, the $T_m$ is 65° C.

Post-hybridization washes also determine stringency conditions. One set of preferred conditions uses a series of washes starting with 6×SSC, 0.5% SDS at room temperature for 15 minutes (min), then repeated with 2×SSC, 0.5% SDS at 45° C. for 30 minutes, and then repeated twice with 0.2×SSC, 0.5% SDS at 50° C. for 30 minutes. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

Selectivity of hybridization exists when hybridization occurs which is more selective than total lack of specificity. Typically, selective hybridization will occur when there is at least about 55% homology over a stretch of at least about 14/25 nucleotides, preferably at least about 65%, more preferably at least about 75%, and most preferably at least about 90%. See, Kanehisa, M. (1984), Nucleic Acids Res. 12:203-

213, which is incorporated herein by reference. Stringent hybridization conditions will typically include salt concentrations of less than about 1 M, more usually less than about 500 mM and preferably less than about 200 mM. Temperature conditions will typically be greater than 20 degrees Celsius, more usually greater than about 30 degrees Celsius and preferably in excess of about 37 degrees Celsius. As other factors may significantly affect the stringency of hybridization, including, among others, base composition and size of the complementary strands, presence of organic solvents and extent of base mismatching, the combination of parameters is more important than the absolute measure of any one.

In a specific embodiment of the invention, polynucleotides of the invention are detected by employing hybridization conditions comprising a hybridization step in less than 500 mM salt and at least 37 degrees Celsius, and a washing step in 2×SSPE at least 63 degrees Celsius. In a preferred embodiment, the hybridization conditions comprise less than 200 mM salt and at least 37 degrees Celsius for the hybridization step. In a more preferred embodiment, the hybridization conditions comprise 2×SSPE and 63 degrees Celsius for both the hybridization and washing steps.

In one embodiment, the length for a hybridizable nucleic acid is at least about 10 nucleotides. Preferable a minimum length for a hybridizable nucleic acid is at least about 15 nucleotides; more preferably at least about 20 nucleotides; and even more preferably the length is at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a nucleic acid, generally of at least 18 nucleotides, that is hybridizable to a genomic DNA molecule, a cDNA molecule, a plasmid DNA or an mRNA molecule. Oligonucleotides can be labeled, e.g., with $^{32}$P-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

"Polymerase chain reaction" is abbreviated PCR and means an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and means an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" is a double-stranded DNA sequence that is transcribed and translated into a polypeptide in a cell in vitro or in vivo when placed under the control of appropriate regulatory sequences. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and means a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 0.5° end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (←—→) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→←) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→→) or (5→3'5'→3').

The term "downstream" refers to a nucleotide sequence that is located 3' to reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include but are not limited to retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" is a "replicon", which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

Vectors may be introduced into the desired host cells by methods known in the art, e.g., transfection, electroporation, microinjection, transduction, cell fusion, DEAE dextran, calcium phosphate precipitation, lipofection (lysosome fusion), particle bombardment, use of a gene gun, or a DNA vector transporter (see, e.g., Wu et al., 1992, J. Biol. Chem. 267: 963-967; Wu and Wu, 1988, J. Biol. Chem. 263: 14621-14624; and Hartmut et al., Canadian Patent Application No. 2,012,311, filed Mar. 15, 1990).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et al., 1987, Proc. Natl. Acad. Sci. U.S.A. 84: 7413; Mackey, et al., 1988, Proc. Natl. Acad. Sci. U.S.A. 85: 8027-8031; and Ulmer et al., 1993, Science 259: 1745-1748). The use of cationic lipids may promote encapsulation of negatively charged nucleic acids, and also promote fusion with negatively charged cell membranes (Felgner and Ringold, 1989, Science 337: 387-388). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g. WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., 1992, Hum Gene Ther. 3: 147-154; and Wu and Wu, 1987, J. Biol. Chem. 262: 4429-4432).

The term "transfection" means the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "genetic region" will refer to a region of a nucleic acid molecule or a nucleotide sequence that comprises a gene encoding a polypeptide.

In addition, the recombinant vector comprising a polynucleotide according to the invention may include one or more origins for replication in the cellular hosts in which their amplification or their expression is sought, markers or selectable markers.

The term "selectable marker" means an identifying factor, usually an antibiotic or chemical resistance gene, that is able to be selected for based upon the marker gene's effect, i.e., resistance to an antibiotic, resistance to a herbicide, calorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Selectable marker genes may also be considered reporter genes.

The term "reporter gene" means a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". Promoters that cause a gene to be expressed in a specific cell type are commonly referred to as "cell-specific promoters" or "tissue-specific promoters". Promoters that cause a gene to be expressed at a specific stage of development or cell differentiation are commonly referred to as "developmentally-specific promoters" or "cell differentiation-specific promoters". Promoters that are induced and cause a gene to be expressed following exposure or treatment of the cell with an agent, biological molecule, chemical, ligand, light, or the like that induces the promoter are commonly referred to as "inducible promoters" or "regulatable promoters". It is further recognized that since in most cases the exact boundaries of regulatory sequences have not been completely defined, DNA fragments of different lengths may have identical promoter activity.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "response element" means one or more cis-acting DNA elements which confer responsiveness on a promoter mediated through interaction with the DNA-binding domains of the first chimeric gene. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the first hybrid protein binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANTGAC/ACYY (see Cherbas L., et. al., (1991), *Genes Dev.* 5, 120-131); AGGTCAN$_{(n)}$AGGTCA, where N$_{(n)}$ can be one or more spacer nucleotides (see D'Avino P P., et. al., (1995), *Mol. Cell. Endocrinol,* 113, 1-9);

and GGGTTGAATGAATTT (see Antoniewski C., et. al., (1994). Mol. Cell Biol. 14, 4465-4474).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid or polynucleotide. Expression may also refer to translation of mRNA into a protein or polypeptide.

The terms "cassette", "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and an EcR-based gene expression system which, in the presence of one or more ligands, modulates the expression of a gene into which the response element and promoter are incorporated.

The terms "modulate" and "modulates" mean to induce, reduce or inhibit nucleic acid or gene expression, resulting in the respective induction, reduction or inhibition of protein or polypeptide production.

The plasmids or vectors according to the invention may further comprise at least one promoter suitable for driving expression of a gene in a host cell. The term "expression vector" means a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving these genes is suitable for the present invention including but not limited to: viral promoters, bacterial promoters, animal promoters, mammalian promoters, synthetic promoters, constitutive promoters, tissue specific promoter, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in Saccharomyces); AOX1 promoter (useful for expression in Pichia); β-lactamase, lac, ara, tet, trp, $IP_L$, $IP_R$, T7, tac, and trc promoters (useful for expression in Escherichia coli); light regulated-, seed specific-, pollen specific-, ovary specific-, pathogenesis or disease related-, cauliflower mosaic virus 35S, CMV 35S minimal, cassaya vein mosaic virus (Cs-VMV), chlorophyll a/b binding protein, ribulose 1,5-bisphosphate carboxylase, shoot-specific, root specific, chitinase, stress inducible, rice tungro bacilliform virus, plant superpromoter, potato leucine aminopeptidase, nitrate reductase, mannopine synthase, nopaline synthase, ubiquitin, zein protein, and anthocyanin promoters (useful for expression in plant cells); animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

Termination control regions, i.e., terminator or polyadenylation sequences, may also be derived from various genes native to the preferred hosts. Optionally, a termination site may be unnecessary, however, it is most preferred if included. In a preferred embodiment of the invention, the termination control region may be comprise or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" means a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" is a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

A "polypeptide" is a polymeric compound comprised of covalently linked amino acid residues. Amino acids have the following general structure:

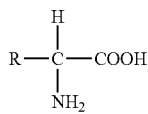

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

A "protein" is a polypeptide that performs a structural or functional role in a living cell.

An "isolated polypeptide" or "isolated protein" is a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A "fragment" of a polypeptide according to the invention will be understood to mean a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2-300 amino acids.

A "heterologous protein" refers to a protein not naturally produced in the cell.

A "mature protein" refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50: 667.). Such proteins (and their encoding genes) have sequence homology, as reflected by their high degree of sequence similarity. However, in common usage and in the instant application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., 1987, Cell 50: 667).

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Sambrook et al., 1989, supra.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the instant invention are those nucleic acid fragments whose DNA sequences are at least 70% identical to the DNA sequence of the nucleic acid fragments reported herein. Preferred substantially nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Even more preferred are nucleic acid fragments that are at least 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Palcage, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215: 403-410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNAS- TAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

Polynucleotides Encoding Whitefly Ecdysone Receptor Polypeptides

The present invention provides novel polynucleotides encoding a whitefly ecdysone receptor polypeptide of the invention, including a full-length whitefly ecdysone receptor protein, and any whitefly ecdysone receptor-specific fragments thereof.

In accordance with specific embodiments of the present invention, nucleic acid sequences encoding portions of a novel ecdysone receptor polypeptide have been elucidated and characterized. Specifically, polynucleotides encoding a homopteran ecdysone receptor from whitefly (BaEcR) has been characterized. The full-length encoding sequence has been determined and is presented herein as nucleotides 102-1349 of SEQ ID NO: 1. In addition, domains within this polynucleotide encoding the full-length BaEcR polypeptide have been defined and are presented herein as described in Table 1.

TABLE 1

Nucleotide and amino acid sequences corresponding to various domains and helices of whitefly ecdysone receptor ("BaEcR").

| Full Length BaEcR or BaEcR Domains | Nucleotides of SEQ ID NO: 1 | Amino Acids of SEQ ID NO: 2 |
|---|---|---|
| A/BCDE (Full length) | 102-1349 | 1-416 |
| A/B | 102-258 | 1-52 |
| C | 259-457 | 53-118 |
| D | 458-677 | 119-192 |
| E | 678-1349 | 193-416 |
| CDE | 259-1349 | 53-416 |
| DE | 458-1349 | 119-416 |
| Helices 1-12 | 648-1349 | 183-416 |

Thus, a first subject of the invention relates to an isolated polynucleotide encoding a novel ecdysone receptor polypeptide. More specifically, the invention relates to an isolated polynucleotide encoding a whitefly ecdysone receptor polypeptide. In a specific embodiment, the isolated polynucleotide comprises a nucleic acid sequence selected from the group consisting of SEQ ID NO: 1, nucleotides 102-1349 of SEQ ID NO: 1, nucleotides 102-258 of SEQ ID NO: 1, nucleotides 259-457 of SEQ ID NO: 1, nucleotides 458-677 of SEQ ID NO: 1, nucleotides 678-1349 of SEQ ID NO: 1, nucleotides 259-1349 of SEQ ID NO: 1, nucleotides 458-1349 of SEQ ID NO: 1, and nucleotides 648-1349 of SEQ ID NO: 1. In another specific embodiment, the isolated polynucleotide comprises a nucleic acid sequence as depicted in SEQ ID NO: 1. In another specific embodiment, the isolated polynucleotide comprises a nucleic acid sequence as depicted in nucleotides 102-1349 of SEQ ID NO: 1. In another specific embodiment, the isolated polynucleotide further comprises a region permitting expression of the polypeptide in a host cell.

The present invention also relates to an isolated polynucleotide encoding a polypeptide comprising an amino acid sequence selected from the group consisting of SEQ ID NO: 2, amino acids 1-52 of SEQ ID NO: 2, amino acids 53-118 of SEQ ID NO: 2, amino acids 119-192 of SEQ ID NO: 2, amino acids 193-416 of SEQ ID NO: 2, amino acids 53-416 of SEQ ID NO: 2, amino acids 119416 of SEQ ID NO: 2, and amino acids 183-416 of SEQ ID NO: 2. In a specific embodiment, the isolated polynucleotide encodes a whitefly ecdysone receptor polypeptide comprising an amino acid sequence as depicted in SEQ ID NO: 2.

The present invention provides novel isolated polynucleotides encoding whitefly ecdysone receptor polypeptides. Having elucidated the sequence and structure of this ecdysone receptor, an isolated polynucleotide encoding a whitefly receptor polypeptide comprising a ligand-binding domain may be used individually or in combination to screen for new ligands that bind this ligand binding domain. Thus, for example, an ecdysone receptor polypeptide according to the invention may be used to control expression of reporter genes for which sensitive assays exist. The ligand binding domain may serve as a reagent for screening new molecules, useful as either agonists or antagonists of the whitefly ecdysone receptor. Either new classes of molecules may be screened, or selected modifications from known ligands may be used. These new ligands find use as highly specific and highly active, naturally occurring pesticides. Thus, the present invention provides for screening for new ligand molecules.

The polynucleotides of the present invention also provide probes for screening for homologous nucleic acid sequences, both in *Bamecia* and other genetic sources. This screening allows isolation of homologous genes from both vertebrates and invertebrates.

Accordingly, any whitefly cell potentially can serve as the nucleic acid source for the molecular cloning of a whitefly ecdysone receptor polynucleotide. The polynucleotide may be obtained by standard procedures known in the art from cloned DNA (e.g., a DNA "library"), and preferably is obtained from a cDNA library prepared from tissues with high level expression of the protein, by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the polynucleotide should be molecularly cloned into a suitable vector for propagation of the polynucleotide.

Once the DNA fragments are generated, identification of the specific DNA fragment containing the desired whitefly ecdysone receptor polynucleotide may be accomplished in a number of ways. For example, DNA fragments may be screened by nucleic acid hybridization to a labeled probe (Benton and Davis, 1977, Science 196: 180; Grunstein and Hogness, 1975, Proc. Natl. Acad. Sci. U.S.A. 72: 3961). Those DNA fragments with substantial homology to the probe will hybridize. As noted above, the greater the degree of homology, the more stringent hybridization conditions can be used.

Further selection can be carried out on the basis of the properties of the polynucleotide, e.g., if the polynucleotide encodes a polypeptide having the isoelectric, electrophoretic, amino acid composition, or partial amino acid sequence of the whitefly ecdysone receptor polypeptide as disclosed herein. Thus, the presence of the polynucleotide may be detected by assays based on the physical, chemical, or immunological properties of its expressed product. For example, cDNA clones, or DNA clones which hybrid-select the proper mRNAs, can be selected which produce a polypeptide that, e.g., has similar or identical electrophoretic migration, isoelectric focusing or non-equilibrium pH gel electrophoresis behavior, proteolytic digestion maps, or antigenic properties as known for a whitefly ecdysone receptor polypeptide. In a specific embodiment, the expressed polypeptide is recognized by a polyclonal antibody that is generated against an epitope specific for a whitefly ecdysone receptor polypeptide.

Due to the degeneracy of nucleotide coding sequences, other polynucleotides that encode substantially the same amino acid sequence as a whitefly ecdysone receptor polynucleotide disclosed herein, including an amino acid sequence that contains a single amino acid variant, may be used in the practice of the present invention. These include but are not limited to allelic genes, homologous genes from other species, and nucleotide sequences comprising all or portions of whitefly ecdysone receptor polynucleotides that are altered by the substitution of different codons that encode the same amino acid residue within the sequence, thus producing a silent change. Likewise, the whitefly ecdysone receptor derivatives of the invention include, but are not limited to, those comprising, as a primary amino acid sequence, all or part of the amino acid sequence of a whitefly ecdysone receptor polypeptide including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations can be produced by various methods known in the art (see Sambrook et al., 1989, infra) and are not expected to affect apparent molecular weight as determined by polyacrylamide gel electrophoresis, or isoelectric point.

The present invention also relates to an isolated whitefly ecdysone receptor polypeptide encoded by a polynucleotide according to the invention.

Whitefly Ecdysone Receptor Polypeptides

The present invention provides novel isolated whitefly ecdysone receptor polypeptides, including a full-length whitefly ecdysone receptor protein, and any whitefly ecdysone receptor-specific polypeptide fragments thereof.

Thus, the invention relates to an isolated ecdysone receptor polypeptide. More specifically, the invention relates to an isolated whitefly ecdysone receptor polypeptide. In a specific embodiment, the isolated ecdysone receptor polypeptide comprises an amino acid sequence selected from the group consisting of SEQ ID NO: 2, amino acids 1-52 of SEQ ID NO: 2, amino acids 53-118 of SEQ ID NO: 2, amino acids 119-192 of SEQ ID NO: 2, amino acids 193-416 of SEQ ID NO: 2, amino acids 53-416 of SEQ ID NO: 2, amino acids 119-416 of SEQ ID NO: 2, and amino acids 183-416 of SEQ ID NO: 2. In another specific embodiment, the isolated ecdysone receptor polypeptide comprises an amino acid sequence as depicted in SEQ ID NO: 2.

In another specific embodiment, the isolated ecdysone receptor polypeptide is encoded by a polynucleotide comprising a nucleic acid sequence selected from the group consisting of SEQ ID NO: 1, nucleotides 102-1349 of SEQ ID NO: 1, nucleotides 102-258 of SEQ ID NO: 1, nucleotides 259-457 of SEQ ID NO: 1, nucleotides 458-677 of SEQ ID NO: 1, nucleotides 678-1349 of SEQ ID NO: 1, nucleotides 259-1349 of SEQ ID NO: 1, nucleotides 458-1349 of SEQ ID NO: 1, and nucleotides 648-1349 of SEQ ID NO: 1. In another specific embodiment, the isolated ecdysone receptor polypeptide is encoded by a polynucleotide comprising a nucleic acid sequence as depicted in SEQ ID NO: 1. In another specific embodiment, the isolated ecdysone receptor polypeptide is encoded by a polynucleotide comprising a nucleic acid sequence as depicted in nucleotides 102-1349 of SEQ ID NO: 1.

One of skill in the art is able to produce other polynucleotides to encode the polypeptides of the invention, by making use of the present invention and the degeneracy or non-universality of the genetic code as described herein.

Additional embodiments of the present invention include an ecdysone receptor polypeptide according to the invention, wherein the ecdysone receptor polypeptide is substantially free of naturally associated cell components. Such polypeptides will typically be either full-length proteins, functional fragments, or fusion proteins comprising segments from an ecdysone receptor polypeptide of the present invention fused to a heterologous, or normally non-contiguous, protein domain. Preferably, the ecdysone receptor polypeptide comprises a transactivation domain, a DNA binding domain, a ligand binding domain, a hinge region, or a heterodimerization domain. More preferably, the ecdysone receptor polypeptide comprises a ligand binding domain that is capable of binding to a ligand selected from the group consisting of a steroid ligand and a non-steroid ligand. As desired, the ecdysone receptor polypeptide may be fused to a second polypeptide to generate a hybrid polypeptide. Preferably, the second polypeptide is a heterologous polypeptide from the steroid hormone nuclear receptor superfamily.

Besides substantially full-length polypeptides, the present invention provides for biologically active fragments of the polypeptides. Significant biological activities include transactivation activity, ligand binding, DNA binding, heterodimerization activity, immunological activity and other biological activities characteristic of steroid receptor superfamily members immunological activities include both immunogenic function in a target immune system, as well as sharing of immunological epitopes for binding, serving as either a competitor or substitute antigen for an ecdysone receptor epitope.

For example, transactivation, ligand binding, or DNA-binding domains may be "swapped" between different new fusion polypeptides or fragments. Thus, novel hybrid polypeptides exhibiting new combinations of specificities result from the functional linkage of transactivation, ligand-binding specificities, or DNA-binding domains. This is extremely useful in the design of inducible expression systems.

For immunological purposes, immunogens may be produced that tandemly repeat polypeptide segments, thereby producing highly antigenic proteins. Alternatively, such polypeptides will serve as highly efficient competitors for specific binding. Production of antibodies to BaEcR is described below.

The present invention also provides for other polypeptides comprising fragments of BaEcR Thus, fusion polypeptides between the BaEcR segments and other homologous or heterologous proteins are provided. Homologous polypeptides may be fusions between different steroid receptor superfamily members, resulting in, for instance, a hybrid protein exhibiting ligand specificity of one member and DNA-binding specificity of another. Likewise, heterologous fusions may be constructed which would exhibit a combination of properties or activities of the derivative proteins. Typical examples are fusions of a reporter polypeptide, e.g., luciferase, with another domain of a receptor, e.g., a DNA-binding domain, so that the presence or location of a desired ligand may be easily determined. See, e.g., Dull et al., U.S. Pat. No. 4,859,609, which is hereby incorporated herein by reference. Other typical gene fusion partners include "zinc finger" segment swapping between DNA-binding proteins, bacterial beta-galactosidase, trpE Protein A, beta-lactamase, alpha amylase, alcohol dehydrogenase and yeast alpha mating factor. See, e.g., Godowski et al. (1988), Science 241: 812-816.

Thus, the present invention also provides an isolated polypeptide selected from the group consisting of a) an isolated polypeptide comprising a transactivation domain, a DNA-binding domain, and a whitefly ecdysone receptor ligand binding domain; b) an isolated polypeptide comprising a DNA-binding domain and a whitefly ecdysone receptor ligand binding domain; and c) an isolated polypeptide comprising a transactivation domain and a whitefly ecdysone receptor ligand binding domain. Preferably, the whitefly ecdysone receptor ligand binding domain comprises an amino acid sequence selected from the group consisting of SEQ ID NO: 2, amino acids 193-416 of SEQ ID NO: 2, amino acids 53-416 of SEQ ID NO: 2, amino acids 119-416 of SEQ ID NO: 2, and amino acids 183-416 of SEQ ID NO: 2. In another preferred embodiment, the whitefly ecdysone receptor ligand binding domain is encoded by a polynucleotide comprising a nucleic acid sequence selected from the group consisting of SEQ ID NO: 1, nucleotides 102-1349 of SEQ ID NO: 1, nucleotides 678-1349 of SEQ ID NO: 1, nucleotides 259-1349 of SEQ ID NO: 1, nucleotides 458-1349 of SEQ ID NO: 1, and nucleotides 648-1349 of SEQ ID NO: 1.

The present invention also provides an isolated hybrid polypeptide selected from the group consisting of a) an isolated hybrid polypeptide comprising a transactivation domain, a DNA-binding domain, and a whitefly ecdysone receptor ligand binding domain; b) an isolated hybrid polypeptide comprising a DNA-binding domain and a whitefly ecdysone receptor ligand binding domain; and c) an isolated hybrid polypeptide comprising a transactivation domain and a whitefly ecdysone receptor ligand binding domain. Preferably, the whitefly ecdysone receptor ligand binding domain comprises an amino acid sequence selected from the group consisting of SEQ ID NO: 2, amino acids 193-416 of SEQ ID NO: 2, amino acids 53-416 of SEQ ID NO: 2, amino acids 119-416 of SEQ ID NO: 2, and amino acids 183-416 of SEQ ID NO: 2. In another preferred embodiment, the whitefly ecdysone receptor ligand binding domain is encoded by a polynucleotide comprising a nucleic acid sequence selected from the group consisting of SEQ ID NO: 1, nucleotides 102-1349 of SEQ ID NO: 1, nucleotides 678-1349 of SEQ ID NO: 1, nucleotides 259-1349 of SEQ ID NO: 1, nucleotides 458-1349 of SEQ ID NO: 1, and nucleotides 648-1349 of SEQ ID NO: 1.

The present invention also relates to compositions comprising an isolated polypeptide according to the invention.

Compositions

The present invention also relates to compositions comprising the isolated polynucleotides or polypeptides according to the invention. Such compositions may comprise a whitefly ecdysone receptor polypeptide or a polynucleotide encoding a whitefly ecdysone receptor polypeptide, as defined above, and an acceptable carrier or vehicle. The compositions of the invention are particularly suitable for formulation of biological material for use in a gene expression modulation system or a ligand-screening assay according to the invention. Thus, in a preferred embodiment, the composition comprises a polynucleotide encoding a whitefly ecdysone receptor polypeptide. In another preferred embodiment, the composition comprises a whitefly ecdysone receptor polypeptide according to the invention.

The phrase "acceptable" refers to molecular entities and compositions that are physiologically tolerable to the cell or organism when administered. The term "carrier" refers to a diluent, adjuvant, excipient, or vehicle with which the composition is administered. Such carriers can be sterile liquids, such as water and oils, including those of petroleum, animal, vegetable or synthetic origin, such as peanut oil, soybean oil, mineral oil, sesame oil and the like. Examples of acceptable carriers are saline, buffered saline, isotonic saline (e.g., monosodium or disodium phosphate, sodium, potassium, calcium or magnesium chloride, or mixtures of such salts), Ringer's solution, dextrose, water, sterile water, glycerol, ethanol, and combinations thereof. 1,3-butanediol and sterile fixed oils are conveniently employed as solvents or suspending media. Any bland fixed oil can be employed including synthetic mono- or di-glycerides. Fatty acids such as oleic acid also find use in the preparation of injectables. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin. Pharmaceutical compositions of the invention may be formulated for the purpose of topical, oral, parenteral, intranasal, intravenous, intramuscular, subcutaneous, intraocular, and the like, administration.

Preferably, the compositions comprise an acceptable vehicle for an injectable formulation. This vehicle can be, in particular, a sterile, isotonic saline solution (monosodium or disodium phosphate, sodium, potassium, calcium or magnesium chloride, and the like, or mixtures of such salts), or dry, in particular lyophilized, compositions which, on addition, as appropriate, of sterilized water or of physiological saline, enable injectable solutions to be formed. The preferred sterile injectable preparations can be a solution or suspension in a nontoxic parenterally acceptable solvent or diluent.

In yet another embodiment, a composition comprising a whitefly ecdysone receptor polypeptide, or polynucleotide encoding the polypeptide, can be delivered in a controlled release system. For example, the polynucleotide or polypeptide may be administered using intravenous infusion, an implantable osmotic pump, a transdemmal patch, liposomes, or other modes of administration. Other controlled release systems are discussed in a review by Langer [*Science* 249: 1527-1533 (1990)].

Expression of Whitefly Ecdysone Receptor Polypeptides

With the sequence of the receptor polypeptides and the polynucleotides encoding them, large quantities of whitefly ecdysone receptor polypeptides may be prepared. By the appropriate expression of vectors in cells, high efficiency production may be achieved. Thereafter, standard purification methods may be used, such as ammonium sulfate precipitations, column chromatography, electrophoresis, centrifugation, crystallization and others. See various volumes of Methods in Enzymology for techniques typically used for protein purification. Alternatively, in some embodiments high efficiency of production is unnecessary, but the presence of a known inducing protein within a carefully engineered expression system is quite valuable. For instance, a combination of: (1) a ligand-responsive enhancer or response element operably linked to (2) a desired gene sequence with (3) the corresponding whitefly ecdysone receptor polypeptide together in an expression system provides a specifically inducible expression system. Typically, the expression system will be a cell, but an in vitro expression system may also be constructed.

A polynucleotide encoding a whitefly ecdysone receptor, or fragment, derivative or analog thereof, or a functionally active derivative, including a chimeric protein, thereof, can be inserted into an appropriate expression vector, i.e., a vector which comprises the necessary elements for the transcription and translation of the inserted protein-coding sequence. Thus, the polynucleotide of the invention is operationally linked with a transcriptional control sequence in an expression vector of the invention. Both cDNA and genomic sequences can be cloned and expressed under control of such regulatory sequences. An expression vector also preferably includes a replication origin.

The isolated polynucleotides of the invention may be inserted into any appropriate cloning vector. A large number of vector-host systems known in the art may be used. Possible vectors include, but are not limited to, plasmids or modified viruses, but the vector system must be compatible with the host cell used. Examples of vectors include, but are not limited to, *Escherichia coli*, bacteriophages such as lambda derivatives, or plasmids such as pBR322 derivatives or pUC plasmid derivatives, e.g. pGEX vectors, pmal-c, pFLAG, etc. The insertion into a cloning vector can, for example, be accomplished by ligating the polynucleotide into a cloning vector that has complementary cohesive termini. However, if the complementary restriction sites used to fragment the polynucleotide are not present in the cloning vector, the ends of the polynucleotide molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Preferably, the cloned gene is contained on a shuttle vector plasmid, which provides for expansion in a cloning cell, e.g., *E. coli*, and purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2µ plasmid.

In addition, the present invention relates to an expression vector comprising a polynucleotide according the invention, operatively linked to a transcription regulatory element. Preferably, the polynucleotide is operatively linked with an expression control sequence permitting expression of the nuclear receptor ligand binding domain in an expression competent host cell. The expression control sequence may comprise a promoter that is functional in the host cell in which expression is desired. The vector may be a plasmid DNA molecule or a viral vector. Preferred viral vectors include retrovirus, adenovirus, adeno-associated virus, herpes virus, and vaccinia virus. The invention further relates to a replication defective recombinant virus comprising in its genome, a polynucleotide according to the invention. Thus, the present invention also relates to an isolated host cell comprising such an expression vector, wherein the transcription regulatory element is operative in the host cell.

The desired genes will be inserted into any of a wide selection of expression vectors. The selection of an appropriate vector and cell line depends upon the constraints of the desired product. Typical expression vectors are described in Sambrook et al. (1989). Suitable cell lines may be selected from a depository, such as the ATCC. See, ATCC Catalogue of Cell Lines and Hybridomas (6th ed.) (1988); ATCC Cell Lines, Viruses, and Antisera, each of which is hereby incorporated herein by reference. The vectors are introduced to the desired cells by standard transformation or transfection procedures as described, for instance, in Sambrook et al. (1989).

Fusion proteins will typically be made by either recombinant nucleic acid methods or by synthetic polypeptide methods. Techniques for nucleic acid manipulation are described generally, for example, in Sambrook et al. (1989), Molecular Cloning: A Laboratory Manual (2d ed.), Vols. 1-3, Cold Spring Harbor Laboratory, which are incorporated herein by reference. Techniques for synthesis of polypeptides are described, for example, in Merrifield, J. Amer. Chem Soc. 85: 2149-2156 (1963).

The nucleotide sequences used to produce fusion proteins of the present invention may be derived from natural or synthetic sequences. Many natural gene sequences are obtainable from various cDNA or from genomic libraries using appropriate probes. See, GenBank™, National Institutes of Health. Typical probes for whitefly ecdysone receptors may be selected from the sequences of Table 1 in accordance with standard procedures. Suitable synthetic DNA fragments may be prepared by the phosphoramidite method described by Beaucage and Carruthers, Tetra. Letts. 22: 1859-1862 (1981). A double stranded fragment may then be obtained either by synthesizing the complementary strand and annealing the strand together under appropriate conditions or by adding the complementary strand using DNA polymerase with an appropriate primer sequence.

The natural or synthetic polynucleotide fragments encoding a desired whitefly ecdysone receptor polypeptide fragment will be incorporated into nucleic acid constructs capable of introduction to and expression in an in vitro cell culture. Usually the nucleic acid constructs will be suitable for replication in a unicellular host, such as yeast or bacteria, but may also be intended for introduction to, with and without and integration within the genome, cultured mammalian or plant or other eukaryotic cell lines. Nucleic acid constructs prepared for introduction into bacteria or yeast will typically include a replication system recognized by the host, the intended DNA fragment encoding the desired receptor polypeptide, transcription and translational initiation regulatory sequences operably linked to the polypeptide encoding segment and transcriptional and translational termination regulatory sequences operably linked to the polypeptide encoding segment. The transcriptional regulatory sequences will typically include a heterologous enhancer, response element, or promoter which is recognized by the host. The selection of an appropriate promoter will depend upon the host, but promoters such as the trp, lac and phage promoters, tRNA promoters and glycolytic enzyme promoters are known. See, Sambrook et al. (1989). Conveniently available expression vectors which include the replication system and transcriptional and translational regulatory sequences together with the insertion site for the steroid receptor DNA sequence may be employed. Examples of workable combinations of cell lines and expression vectors are described in Sambrook et al. (1989); see also, Metzger et al. (1988), Nature 334: 31-36.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification of proteins. Appropriate cell lines or host systems can be chosen to ensure the desired modification and processing of the foreign protein expressed. Expression in yeast can produce a biologically active product. Expression in eukaryotic cells can increase the likelihood of "native" folding. Moreover, expression in mammalian cells can provide a tool for reconstituting, or constituting, whitefly ecdysone receptor activity. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), particle bombardment, use of a gene gun, or a DNA vector transporter (see, e.g., Wu et al., 1992, J. Biol. Chem. 267:963-967; Wu and Wu, 1988, J. Biol. Chen. 263:14621-14624; Hartmut et al., Canadian Patent Application No. 2,012,311, filed Mar. 15, 1990).

Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

Vectors and Gene Expression Cassettes Comprising a Whitefly Ecdysone Receptor Polynucleotide Thus, the present invention also relates to a vector comprising a polynucleotide encoding a whitefly ecdysone receptor polypeptide according to the invention. The present invention also provides a gene expression cassette comprising a polynucleotide encoding a whitefly ecdysone receptor polypeptide according to the invention. The polynucleotides of the invention, where appropriate incorporated in vectors or gene expression cassettes, and the compositions comprising them, are useful for regulating gene expression in an ecdysone receptor-based gene expression system. They may be used for the transfer and expression of genes in vitro or in vivo in any type of cell or tissue. The transformation can, moreover, be targeted (transfer to a particular tissue can, in particular, be determined by the choice of a vector, and expression by the choice of a particular promoter). The polynucleotides and vectors of the invention are advantageously used for the production in vivo and intracellularly, of polypeptides of interest.

The polynucleotides encoding the whitefly ecdysone receptor polypeptides of the invention will typically be used in a plasmid vector. Preferably, an expression control sequence is operably linked to the whitefly ecdysone receptor polynucleotide coding sequence for expression of the whitefly ecdysone receptor polypeptide. The expression control sequence may be any enhancer, response element, or promoter system in vectors capable of transforming or transfecting a host cell. Once the vector has been incorporated into the appropriate host, the host, depending on the use, will be maintained under conditions suitable for high-level expression of the polynucleotides.

Polynucleotides will normally be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

*Escherichia coli* is one prokaryotic host useful for cloning the polynucleotides of the present invention. Other microbial hosts suitable for use include bacilli, such as *Bacillus subtilis*, and other enterobacteriaceae, such as *Salmonella, Serratia*, and various *Pseudomonas* species.

Other eukaryotic cells may be used, including yeast cells, insect tissue culture cells, avian cells or the like. Preferably, mammalian tissue cell culture will be used to produce the polypeptides of the present invention (see, Winnacker, From Genes to Clones, VCH Publishers, N.Y. (1987), which is incorporated herein by reference). Yeast and mammalian cells are preferred cells in which to use whitefly ecdysone receptor-based inducible gene expression systems because they naturally lack the molecules which confer responsiveness to the ligands for ecdysone receptor.

Expression vectors may also include expression control sequences, such as an origin of replication, a promoter, an enhancer, a response element, and necessary processing information sites, such as ribosome-binding sites, RNA splice sites, polyadenylation sites, and transcriptional terminator sequences. Preferably, the enhancers or promoters will be those naturally associated with genes encoding the steroid receptors, although it will be understood that in many cases others will be equally or more appropriate. Other preferred expression control sequences are enhancers or promoters derived from viruses, such as SV40, Adenovirus, Bovine Papilloma Virus, and the like.

The vectors comprising the polynucleotides of the present invention can be transferred into the host cell by well-known methods, which vary depending on the type of cellular host. For example, calcium chloride transfection is commonly utilized for procaryotic cells, whereas calcium phosphate treatment may be used for other cellular hosts. (See, generally, Sambrook et al. (1989), Molecular Cloning: A Laboratory Manual (2d ed.), Cold Spring Harbor Press, which is incorporated herein by reference.) The term "transformed cell" is meant to also include the progeny of a transformed cell.

The necessary transcriptional and translational signals can be provided on a recombinant expression vector, or they may be supplied by the native gene encoding whitefly ecdysone receptor and/or its flanking regions. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant whitefly ecdysone receptor protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the polynucleotide encoding whitefly ecdysone receptor is cultured in an appropriate cell culture medium under conditions that provide for expression of whitefly ecdysone receptor by the cell. Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

A polynucleotide encoding a whitefly ecdysone receptor polypeptide may be operably linked and controlled by any regulatory region, i.e., promoter/enhancer element known in the art, but these regulatory elements must be functional in the host cell selected for expression. The regulatory regions may comprise a promoter region for functional transcription in the host cell, as well as a region situated 3' of the gene of interest, and which specifies a signal for termination of transcription and a polyadenylation site. All these elements constitute an expression cassette.

Expression vectors comprising a polynucleotide encoding a whitefly ecdysone receptor polypeptide of the invention can be identified by five general approaches: (a) PCR amplification of the desired plasmid DNA or specific mRNA, (b) nucleic acid hybridization, (c) presence or absence of selection marker gene functions, (d) analyses with appropriate restriction endonucleases, and (e) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding a whitefly ecdysone receptor polypeptide is inserted within the "selection marker" gene sequence of the vector, recombinants comprising the whitefly ecdysone receptor nucleic acid insert can be identified by the absence of the gene function. In the fourth approach, recombinant expression vectors are identified by digestion with appropriate restriction enzymes. In the fifth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and synthetic DNA sequences. Suitable vectors include but are not limited to derivatives of SV40 and known bacterial plasmids, e.g. E. coli plasmids col El, pCR1, pBR322, pMal-C2, pET, pGEX (Smith et al., 1988, Gene 67: 31-40), pMB9 and their derivatives, plasmids such as RP4; phage DNAS, e.g., the numerous derivatives of phage 1, e.g., NM989, and other phage DNA, e.g., M13 and filamentous single stranded phage DNA; yeast plasmids such as the 2m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

The present invention also provides a gene expression cassette that is capable of being expressed in a host cell, wherein the gene expression cassette comprises a polynucleotide that encodes a whitefly ecdysone receptor polypeptide according to the invention. Thus, Applicants' invention also provides novel gene expression cassettes useful in an ecdysone receptor-based gene expression system.

In a specific embodiment, the gene expression cassette that is capable of being expressed in a host cell comprises a polynucleotide that encodes a polypeptide selected from the group consisting of a) a polypeptide comprising a transactivation domain, a DNA-binding domain, and a whitefly ecdysone receptor ligand binding domain; b) a polypeptide comprising a DNA-binding domain and a whitefly ecdysone receptor ligand binding domain; and c) a polypeptide comprising a transactivation domain and a whitefly ecdysone receptor ligand binding domain.

In another specific embodiment, the present invention provides a gene expression cassette that is capable of being expressed in a host cell, wherein the gene expression cassette comprises a polynucleotide that encodes a hybrid polypeptide selected from the group consisting of a) a hybrid polypeptide comprising a transactivation domain, a DNA-binding domain, and a whitefly ecdysone receptor ligand binding domain; b) a hybrid polypeptide comprising a DNA-binding domain and a whitefly ecdysone receptor ligand binding domain; and c) a hybrid polypeptide comprising a transactivation domain and a whitefly ecdysone receptor ligand binding domain. A hybrid polypeptide according to the invention comprises at least two polypeptide fragments, wherein each polypeptide fragment is from a different source, i.e., a different polypeptide, a different nuclear receptor, a different species, etc. The hybrid polypeptide according to the invention may comprise at least two polypeptide domains, wherein each polypeptide domain is from a different source.

Preferably, the whitefly ecdysone receptor ligand binding domain is from a whitefly Bamecia argentifoli EcR ("BaEcR").

In a specific embodiment, the whitefly ecdysone receptor ligand binding domain is encoded by a polynucleotide comprising a nucleic acid sequence selected from the group consisting of SEQ ID NO: 1, nucleotides 102-1349 of SEQ ID NO: 1, nucleotides 678-1349 of SEQ ID NO: 1, nucleotides 259-1349 of SEQ ID NO: 1, nucleotides 458-1349 of SEQ ID NO: 1, and nucleotides 648-1349 of SEQ ID NO: 1.

In a specific embodiment, the whitefly ecdysone receptor ligand binding domain comprises an amino acid sequence selected from the group consisting of SEQ ID NO: 2, amino acids 193-416 of SEQ ID NO: 2, amino acids 53-416 of SEQ ID NO: 2, amino acids 119-416 of SEQ ID NO: 2, and amino acids 183-416 of SEQ ID NO: 2.

The DNA binding domain can be any DNA binding domain with a known response element, including synthetic and chimeric DNA binding domains, or analogs, combinations, or modifications thereof. Preferably, the DBD is a GAL4 DBD, a LexA DBD, a transcription factor DBD, a steroid/thyroid hormone nuclear receptor superfamily member DBD, such as an EcR DBD, or a bacterial LacZ DBD.

The transactivation domain (abbreviated "AD" or "TA") may be any steroid/thyroid hormone nuclear receptor AD, synthetic or chimeric AD, polyglutamine AD, basic or acidic amino acid AD, a VP16 AD, a GALA AD, an NF-κB AD, a BP64 AD, a B42 acidic activation domain (B42AD), a p65 transactivation domain (p65AD), or an analog, combination, or modification thereof. In a specific embodiment, the AD is a synthetic or chimeric AD, or is obtained from an EcR, a glucocorticoid receptor, VP16, GAL4, NF-kB, or B42 acidic activation domain AD.

In a specific embodiment, the gene expression cassette encodes a hybrid polypeptide comprising either a) a DNA-binding domain, or b) a transactivation domain; and a BaEcR ligand binding domain according to the invention.

The present invention also provides a gene expression cassette comprising: i) a response element comprising a domain recognized by a polypeptide comprising a DNA binding domain; ii) a promoter that is activated by a polypeptide comprising a transactivation domain; and iii) a gene whose expression is to be modulated.

The response element ("RE") may be any response element with a known DNA binding domain, or an analog, combination, or modification thereof. A single RE may be employed or multiple REs, either multiple copies of the same RE or two or more different REs, may be used in the present invention. In a specific embodiment, the RE is an RE from GAL4 ("GAL4RE"), LexA, a steroid/thyroid hormone nuclear receptor RE, such as an ecdysone response element (EcRE), or a synthetic RE that recognizes a synthetic DNA binding domain.

A steroid/thyroid hormone nuclear receptor DNA binding domain, activation domain or response element according to the invention may be obtained from a steroid/thyroid hormone nuclear receptor selected from the group consisting of ecdysone receptor (EcR), ubiquitous receptor (UR), orphan receptor 1 (OR-1), steroid hormone nuclear receptor 1 (NER-1), RXR interacting protein-15 (RIP-15), liver x receptor β (LXRβ), steroid hormone receptor like protein (RLD-1), liver x receptor (LXR), liver x receptor α (LXRα), farnesoid x receptor XR), receptor interacting protein 14 (RIP-14), farnesol receptor (HRR-1), thyroid hormone receptor α (TRα), thyroid receptor 1 (c-erbA-1), thyroid hormone receptor β (TRβ), retinoic acid receptor α (RARα), retinoic acid receptor β (RARβ, HAP), retinoic acid receptor γ (RARγ), retinoic acid receptor gamma-like (RARD), peroxisome proliferator-activated receptor α (PPARα), peroxisome proliferator-activated receptor β (PPARβ), peroxisome proliferator-activated receptor δ (PPARδ, NUC-1), peroxisome proliferator-activator related receptor (FFAR), peroxisome proliferator-activated receptor γ (PPARγ), orphan receptor encoded by non-encoding strand of thyroid hormone receptor α (REVERBα), v-erb A related receptor (EAR-1), v-erb related receptor (EAR-1A), γ), orphan receptor encoded by non-encoding strand of thyroid hormone receptor β (REVERBβ), v-erb related receptor (EAR-1β), orphan nuclear receptor BD73 (BD73), rev-erbA-related receptor (RVR), zinc finger protein 126 (HZF2), ecdysone-inducible protein E75 (E75), ecdysone-inducible protein E78 (E78), *Drosophila* receptor 78 (DR-78), retinoid-related orphan receptor α (RORα), retinoid Z receptor α (RZRα), retinoid related orphan receptor β (RORβ), retinoid Z receptor β (RZRβ), retinoid-related orphan receptor γ (RORγ), retinoid Z receptor γ (RZRγ), retinoid-related orphan receptor (TOR), hormone receptor 3 (HR-3), *Drosophila* hormone receptor 3 (DHR-3), *Manduca* hormone receptor 3 (MHR-3), *Gallaria* hormone receptor 3 (GHR-3), *C. elegans* nuclear receptor 3 (CNR-3), *Choristoneura* hormone receptor 3 (CHR-3), *C. elegans* nuclear receptor 14 (CNR-14), vitamin D receptor (VDR), orphan nuclear receptor (ONR-1), pregnane X receptor (PXR), steroid and xenobiotic receptor (SXR), benzoate X receptor (BXR), nuclear receptor (MB-67), constitutive androstane receptor 1 (CAR-1), constitutive androstane receptor α (CARα), constitutive androstane receptor 2 (CAR-2), constitutive androstane receptor β (CARβ), *Drosophila* hormone receptor 96 (DHR-96), nuclear hormone receptor 1 (NHR-1), hepatocyte nuclear factor 4 (HNF-4), hepatocyte nuclear factor 4G (HNF-4G), hepatocyte nuclear factor 4B (HNF-4B), hepatocyte nuclear factor 4D (HNF-4D, DHNF-4), retinoid X receptor α (RXRα), retinoid X receptor β (RXRβ), H-2 region II binding protein (H-2RIIBP), nuclear receptor coregulator-1 (RCOR-1), retinoid X receptor γ (RXRγ), Ultraspiracle (USP), 2C1 nuclear receptor, chorion factor 1 (CF-1), testicular receptor 2 (TR-2), testicular receptor 2-11 (TR2-11), testicular receptor 4 (TR4), TAK-1, *Drosophila* hormone receptor (DHR78), Tailless (TLL), tailless homolog (TLX), XTLL, chicken ovalbumin upstream promoter transcription factor I (COUP-TFI), chicken ovalbuniin upstream promoter transcription factor A (COUP-TFA), EAR-3, SVP44, chicken ovalbumin upstream promoter transcription factor II (COUP-TFII), chicken ovalbumin upstream promoter transcription factor B (COUP-TFB), ARP-1, SVP-40, SVP, chicken ovalbumin upstream promoter transcription factor m (COUP-TFIII), chicken ovalburnin upstream promoter transcription factor G (COUP-TFG), SVP-46, EAR-2, estrogen receptor α (ERα), estrogen receptor β (ERRβ), estrogen related receptor 1 (ERR1), estrogen related receptor α (ERRα), estrogen related receptor 2 (ERR2), estrogen related receptor β (ERRβ), glucocorticoid receptor (GR), mineralocorticoid receptor (MR), progesterone receptor (PR), androgen receptor (AR), nerve growth factor induced gene B (NGFI-B), nuclear receptor similar to Nur-77 (TRS), N10, Orphan receptor (NUR-77), Human early response gene (NAK-1), Nurr related factor 1 (NURR-1), a human immediate-early response gene (NOT), regenerating liver nuclear receptor 1 (RNR-1), hematopoietic zinc finger 3 (HZF-3), Nur related protein −1 (TINOR), Nuclear orphan receptor 1 (NOR-1), NOR1 related receptor (MINOR), *Drosophila* hormone receptor 38 (DHR-38), *C. elegans* nuclear receptor 8 (CNR-8), C48D5, steroidogenic factor 1 (SF1), endozepine-like peptide (ELP), fushi tarazu factor 1 (FTZ-F1), adrenal 4 binding protein (AD4BP), liver receptor homolog (LRH-1), Ftz-F1-related orphan receptor A (xFFrA), Ftz-F1-related orphan receptor B (xFFrB), nuclear receptor related to LRH-1 (FFLR), nuclear receptor related to LRH-1 (PHR), fetoprotein transcription factor (FTF), germ cell nuclear factor (GC-NFM), retinoid receptor-related testis-associated receptor (RTR), knirps (KNI), knirps related (KNRL), Embryonic gonad (EGON), *Drosophila* gene for ligand dependent nuclear receptor (EAGLE), nuclear receptor similar to trithorax (ODR7), Trithorax, dosage sensitive sex reversal adrenal hypoplasia congenita critical region chromosome X gene (DAX-1), adrenal hypoplasia congenita and hypogonadotropic hypogonadism (AHCH), and short heterodimer partner (SHP).

For purposes of this invention, nuclear receptors and whitefly ecdysone receptors also include synthetic and chimeric nuclear receptors and whitefly ecdysone receptors and their homologs.

Antibodies to Whitefly Ecdysone Receptor

According to the invention, a whitefly ecdysone receptor polypeptide produced recombinantly or by chemical synthesis, and fragments or other derivatives or analogs thereof, including fusion proteins, may be used as an antigen or immunogen to generate antibodies. Preferably, the antibodies specifically bind homopteran ecdysone receptor polypeptides, but do not bind other ecdysone receptor polypeptides. More preferably, the antibodies specifically bind a whitefly ecdysone receptor polypeptide, but do not bind other ecdysone receptor polypeptides.

The present invention also relates to antigenic peptides and antibodies thereto. More particularly, the invention relates to antigenic peptides comprising a fragment of a whitefly ecdysone receptor polypeptide according to the invention, wherein the fragment has a property selected from the group consisting of:

(a) it is encoded by a polynucleotide comprising a nucleic acid sequence selected from the group consisting of nucleotides 102-258 of SEQ ID NO: 1, nucleotides 259-457 of SEQ ID NO: 1, nucleotides 458-677 of SEQ ID NO: 1, nucleotides 678-1349 of SEQ ID NO: 1, nucleotides 259-1349 of SEQ ID NO: 1, nucleotides 458-1349 of SEQ ID NO: 1, and nucleotides 648-1349 of SEQ ID NO: 1;

(b) it comprises an amino acid sequence selected from the group consisting of amino acids 1-52 of SEQ ID NO: 2, amino acids 53-118 of SEQ ID NO: 2, amino acids 119-192 of SEQ ID NO: 2, amino acids 193-416 of SEQ ID NO: 2, amino acids 53-416 of SEQ ID NO: 2, amino acids 119-416 of SEQ ID NO: 2, and amino acids 183-416 of SEQ ID NO: 2; and (c) it specifically binds to an antibody generated against an epitope within a polypeptide comprising an amino acid sequence selected from the group consisting of SEQ ID NO: 2, amino acids 1-52 of SEQ ID NO: 2, amino acids 53-118 of SEQ ID NO: 2, amino acids 119-192 of SEQ ID NO: 2, amino acids 193-416 of SEQ ID NO: 2, amino acids 53-416 of SEQ ID NO: 2, amino acids 119-416 of SEQ ID NO: 2, and amino acids 183-416 of SEQ ID NO: 2.

In another embodiment, the invention relates to an antibody which specifically binds an antigenic peptide comprising a fragment of a whitefly ecdysone receptor polypeptide according to the invention as described above. The antibody may be polyclonal or monoclonal and may be produced by in vitro or in vivo techniques.

The antibodies of the invention possess specificity for binding to particular homopteran ecdysone receptors. Thus, reagents for determining qualitative or quantitative presence of these or homologous polypeptides may be produced. Alternatively, these antibodies may be used to separate or purify receptor polypeptides.

For production of polyclonal antibodies, an appropriate target immune system is selected, typically a mouse or rabbit. The substantially purified antigen is presented to the immune system in a fashion determined by methods appropriate for the animal and other parameters well known to immunologists. Typical sites for injection are in the footpads, intramuscularly, intraperitoneally, or intradermally. Of course, another species may be substituted for a mouse or rabbit.

An immunological response is usually assayed with an immunoassay. Normally such immunoassays involve some purification of a source of antigen, for example, produced by the same cells and in the same fashion as the antigen was produced. The immunoassay may be a radioimmunoassay, an enzyme-linked assay (ELISA), a fluorescent assay, or any of many other choices, most of which are functionally equivalent but may exhibit advantages under specific conditions.

Monoclonal antibodies with high affinities are typically made by standard procedures as described, e.g., in Harlow and Lane (1988), Antibodies: A Laboratory Manual, Cold Spring Harbor Laboratory; or Goding (1986), Monoclonal Antibodies: Principles and Practice (2d ed) Academic Press, New York, which are hereby incorporated herein by reference. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone are tested for their production of an appropriate antibody specific for the desired region of the antigen.

Other suitable techniques involve in vitro exposure of lymphocytes to the antigenic polypeptides or alternatively to selection of libraries of antibodies in phage or similar vectors. See, Huse et al., (1989) "Generation of a Large Combinatorial Library of the Immunoglobulin Repertoire in Phage Lambda," Science 246: 1275-1281, hereby incorporated herein by reference.

The polypeptides and antibodies of the present invention may be used with or without modification. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescence, chemiluminescence, magnetic particles and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10 amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

Such antibodies include but are not limited to polyclonal, monoclonal, chimeric, single chain, Fab fragments, and a Fab expression library. The anti-whitefly ecdysone receptor antibodies of the invention may be cross-reactive, e.g., they may recognize whitefly ecdysone receptor from different species. Polyclonal antibodies have greater likelihood of cross reactivity. Alternatively, an antibody of the invention may be specific for a single form of whitefly ecdysone receptor, such as whitefly ecdysone receptor. Preferably, such an antibody is specific for whitefly ecdysone receptor.

Various procedures known in the art may be used for the production of polyclonal antibodies. For the production of antibody, various host animals can be immunized by injection with the whitefly ecdysone receptor polypeptide, or a derivative (e.g., fragment or fusion protein) thereof, including but not limited to rabbits, mice, rats, sheep, goats, etc. In one embodiment, the whitefly ecdysone receptor polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the whitefly ecdysone receptor polypeptide, or fragment, analog, or derivative thereof, any technique that provides for the production of antibody molecules by continuous cell lines in culture may be used. These include but are not limited to the hybridoma technique originally developed by Kohler and Milstein [*Nature* 256: 495497 (1975)], as well as the trioma technique, the human B-cell hybridoma technique [Kozbor et al., *Immunology Today* 4: 72 1983); Cote et al., *Proc. Natl. Acad. Sci. U.S.A.* 80: 2026-2030 (1983)], and the EBV-hybridoma technique to produce human monoclonal antibodies [Cole et al., in *Monoclonal Antibodies and Cancer Therapy*, Alan R. Liss, Inc., pp. 77-96 (1985)]. In an additional embodiment of the invention, monoclonal antibodies can be produced in germ-free animals [International Patent Publication No. WO 89/12690, published 28 Dec. 1989]. In fact, according to the invention, techniques developed for the production of "chimeric antibodies" [Morrison et al., *J. Bacteriol.* 159: 870 (1984); Neuberger et al., *Nature* 312: 604-608 (1984); Takeda et al., *Nature* 314: 452-454 (1985)] by splicing the genes from a mouse antibody molecule specific for a whitefly ecdysone receptor polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain Fv (scFv) antibodies [U.S. Pat. Nos. 5,476,786 and 5,132,405 to Huston; U.S. Pat. No. 4,946,778] can be adapted to produce whitefly ecdysone receptor polypeptide-specific single chain antibodies. An additional embodiment of the invention utilizes the techniques described for the construction of Fab expression libraries [Huse et al., *Science* 246: 1275-1281 (1989)] to allow rapid and easy identification of monoclonal Fab fragments with the desired specificity for a whitefly ecdysone receptor polypeptide, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a whitefly ecdysone receptor polypeptide, one may assay generated hybridomas for a product which binds to a whitefly ecdysone receptor polypeptide fragment containing such epitope. For selection of an antibody specific to a whitefly ecdysone receptor polypeptide from a particular species of animal, one can select on the basis of positive binding with whitefly ecdysone receptor polypeptide expressed by or isolated from cells of that species of animal.

The foregoing antibodies can be used in methods known in the art relating to the localization and activity of the whitefly ecdysone receptor polypeptide, e.g., for western blotting, imaging whitefly ecdysone receptor polypeptide in situ, measuring levels thereof in appropriate physiological samples, etc. using any of the detection techniques mentioned above or known in the art.

In a specific embodiment, antibodies that agonize or antagonize the activity of whitefly ecdysone receptor polypeptide can be generated. Such antibodies can be tested using the assays described infra for identifying ligands. In particular, such antibodies can be scFv antibodies expressed intracellularly.

Uses of Novel Polynucleotides and Polypeptides of the Invention

The present invention further provides a number of uses for the whitefly ecdysone receptor polynucleotides of the present invention and their encoded polypeptides.

The whitefly ecdysone receptor polypeptides of the present invention have a variety of utilities. For example, the polynucleotides and polypeptides of the invention are useful in methods of modulating gene expression in an ecdysone receptor-based gene expression system. Also included are methods for identifying and selecting ligands specific for binding to a ligand binding domain of a polypeptide of the invention, methods for identifying and selecting compounds exhibiting specific binding to the ligand binding domain and methods for modulating insect physiology or development (e.g., killing).

Methods of Modulating Gene Expression

As presented herein, Applicants' novel polynucleotides and polypeptides are useful in an ecdysone receptor-based gene expression system to provide a regulatable gene expression system in both prokaryotic and eukaryotic host cells. Thus, the present invention also relates to the use of the novel whitefly ecdysone receptor polynucleotides and polypeptides of the present invention in an ecdysone receptor-based gene expression system, and methods of modulating the expression of a gene within a host cell using such an ecdysone receptor-based gene expression system.

This gene expression system may be a "single switch"-based gene expression system in which the transactivation domain, DNA-binding domain and ligand binding domain are on one encoded polypeptide. Alternatively, the gene expression modulation system may be a "dual switch"- or "two-hybrid"-based gene expression modulation system in which the transactivation domain and DNA-binding domain are located on two different encoded polypeptides. Applicants' have demonstrated for the first time that whitefly ecdysone receptor polynucleotides and polypeptides of the invention can be used as a component of an ecdysone receptor-based inducible gene expression system to modify gene expression in a host cell.

In particular, the present invention relates to a gene expression modulation system comprising at least one gene expression cassette that is capable of being expressed in a host cell comprising a polynucleotide that encodes a whitefly ecdysone receptor polypeptide. Preferably, the whitefly ecdysone receptor polypeptide comprises an amino acid sequence selected from the group consisting of SEQ ID NO: 2, amino acids 1-52 of SEQ ID NO: 2, amino acids 53-118 of SEQ ID NO: 2, amino acids 119-192 of SEQ ID NO: 2, amino acids 193-416 of SEQ ID NO: 2, amino acids 53-416 of SEQ ID NO: 2, amino acids 119-416 of SEQ ID NO: 2, and amino acids 183-416 of SEQ ID NO: 2. More preferably, the whitefly ecdysone receptor polypeptide comprises amino acids 193-416 of SEQ ID NO: 2, amino acids 53-416 of SEQ ID NO: 2, amino acids 119-416 of SEQ ID NO: 2, or amino acids 183-416 of SEQ ID NO: 2.

In a specific embodiment, the gene expression modulation system comprises a gene expression cassette comprising a polynucleotide that encodes a polypeptide comprising a transactivation domain, a DNA-binding domain that recognizes a response element associated with a gene whose expression is to be modulated; and a whitefly ecdysone receptor ligand binding domain (referred to herein as "BaEcR LBD"). The gene expression modulation system may further comprise a second gene expression cassette comprising: i) a response element recognized by the DNA-binding domain of the encoded polypeptide of the first gene expression cassette; ii) a promoter that is activated by the transactivation domain of the encoded polypeptide of the first gene expression cassette; and iii) a gene whose expression is to be modulated.

In another specific embodiment, the gene expression modulation system comprises a gene expression cassette comprising a) a polynucleotide that encodes a polypeptide comprising a transactivation domain, a DNA-binding domain that recognizes a response element associated with a gene whose expression is to be modulated; and an BaEcR LBD, and b) a second nuclear receptor ligand binding domain selected from the group consisting of a vertebrate retinoid X receptor ligand binding domain, an invertebrate retinoid X receptor ligand binding domain, an ultraspiracle protein ligand binding domain, and a chimeric ligand binding domain comprising two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, invertebrate retinoid X receptor ligand binding domain, or ultraspiracle protein ligand binding domain. The gene expression modulation system may further comprise a second gene expression cassette comprising: i) a response element recognized by the DNA-binding domain of the encoded polypeptide of the first gene expression cassette; ii) a promoter that is activated by the transactivation domain of the encoded polypeptide of the first gene expression cassette; and iii) a gene whose expression is to be modulated.

In another specific embodiment, the gene expression modulation system comprises a first gene expression cassette comprising a polynucleotide that encodes a first polypeptide comprising a DNA-binding domain that recognizes a response element associated with a gene whose expression is to be modulated and a nuclear receptor ligand binding domain, and a second gene expression cassette comprising a polynucleotide that encodes a second polypeptide comprising a transactivation domain and a nuclear receptor ligand binding domain, wherein one of the nuclear receptor ligand binding domains is an BaEcR LBD. In a preferred embodiment, the first polypeptide is substantially free of a transactivation domain and the second polypeptide is substantially free of a DNA binding domain. For purposes of the invention, "substantially free of a DNA binding domain" means that the protein in question does not contain a sufficient sequence of the domain in question to provide activation or binding activity. The gene expression modulation system may further comprise a third gene expression cassette comprising: i) a response element recognized by the DNA-binding domain of the first polypeptide of the first gene expression cassette; ii) a promoter that is activated by the transactivation domain of the second polypeptide of the second gene expression cassette; and iii) a gene whose expression is to be modulated.

Wherein when only one nuclear receptor ligand binding domain is an BaEcR LBD, the other nuclear receptor ligand binding domain may be from any other nuclear receptor that forms a dimer with the BaEcR LBD. For example, the other nuclear receptor ligand binding domain ("partner") may be from another ecdysone receptor, a vertebrate retinoid X receptor (RXR), an invertebrate RXR, an ultraspiracle protein (USP), or a chimeric nuclear receptor comprising at least two different nuclear receptor ligand binding domain polypeptide fragments selected from the group consisting of a vertebrate RXR, an invertebrate RXR, and a USP (see co-pending applications PCT/US01/09050, U.S. 60/294,814, and U.S. 60/294,819, incorporated herein by reference in their entirety). The "partner" nuclear receptor ligand binding domain may further comprise a truncation mutation, a deletion mutation, a substitution mutation, or another modification.

In a specific embodiment, the whitefly ecdysone receptor ligand binding domain comprises an amino acid sequence selected from the group consisting of SEQ ID NO: 2, amino acids 193-416 of SEQ ID NO: 2, amino acids 53-416 of SEQ ID NO: 2, amino acids 119-416 of SEQ ID NO: 2, and amino acids 183-416 of SEQ ID NO: 2. In another embodiment, the whitefly ecdysone receptor ligand binding domain is encoded by a polynucleotide comprising a nucleic acid sequence selected from the group consisting of SEQ ID NO: 1, nucleotides 102-1349 of SEQ ID NO: 1, nucleotides 678-1349 of SEQ ID NO: 1, nucleotides 259-1349 of SEQ ID NO: 1, nucleotides 458-1349 of SEQ ID NO: 1, and nucleotides 648-1349 of SEQ ID NO: 1.

In a specific embodiment, the gene whose expression is to be modulated is a homologous gene with respect to the host cell. In another specific embodiment, the gene whose expression is to be modulated is a heterologous gene with respect to the host cell.

The ligands for use in the methods of modulating gene expression are described below, when combined with the ligand binding domain of the nuclear receptor(s), which in turn are bound to the response element linked to a gene, provide the means for external temporal regulation of expression of the gene. The binding mechanism or the order in which the various components of this invention bind to each other, that is, for example, ligand to ligand binding domain, DNA-binding domain to response element, transactivation domain to promoter, etc., is not critical.

Thus, Applicants' invention is useful in methods of modulating gene expression in a host cell using a whitefly ecdysone receptor according to the invention. Specifically, Applicants' invention provides a method of modulating the expression of a gene in a host cell comprising the steps of: a) introducing into the host cell an ecdysone receptor-based gene expression modulation system comprising a whitefly ecdysone receptor according to the invention; and b) introducing into the host cell a ligand; wherein the gene to be modulated is a component of a gene expression cassette comprising: i) a response element comprising a domain recognized by the DNA binding domain of the gene expression system; ii) a promoter that is activated by the transactivation domain of the gene expression system; and iii) a gene whose expression is to be modulated, whereby upon introduction of the ligand into the host cell, expression of the gene is modulated.

The invention also provides a method of modulating the expression of a gene in a host cell comprising the steps of: a) introducing into the host cell an ecdysone receptor-based gene expression modulation system comprising a whitefly ecdysone receptor according to the invention; b) introducing into the host cell a gene expression cassette, wherein the gene expression cassette comprises i) a response element comprising a domain recognized by the DNA binding domain from the gene expression system; ii) a promoter that is activated by the transactivation domain of the gene expression system; and iii) a gene whose expression is to be modulated; and c) introducing into the host cell a ligand; whereby upon introduction of the ligand into the host cell, expression of the gene is modulated.

Genes of interest for expression in a host cell using Applicants' methods may be endogenous genes or heterologous genes. Nucleic acid or amino acid sequence information for a desired gene or protein can be located in one of many public access databases, for example, GENBANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in the methods described herein.

Examples of genes of interest for expression in a host cell using these methods include, but are not limited to: antigens produced in plants as vaccines, enzymes like alpha-amylase, phytase, glucanes, xylase and xylanase, genes for resistance against insects, nematodes, fungi, bacteria, viruses, and abiotic stresses, nutraceuticals, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, genes encoding therapeutically desirable polypeptides or products that may be used to treat a condition, a disease, a disorder, a dysfunction, a genetic defect, such as monoclonal antibodies, enzymes, proteases, cytokines, interferons, insulin, erthropoietin, clotting factors, other blood factors or components, viral vectors for gene therapy, virus for vaccines, targets for drug discovery, functional genomics, and proteomics analyses and applications, and the like.

The term "ligand" is meant herein to refer to a molecule that binds the domain described here as the "ligand binding domain." Also, a ligand for a whitefly ecdysone receptor is a ligand which serves either as the natural ligand to which the ecdysone receptor binds, or a functional analogue which may serve as an agonist or antagonist.

Acceptable ligands are any that modulate expression of the gene when binding of the DNA binding domain of the gene expression system according to the invention to the response element in the presence of the ligand results in activation or suppression of expression of the genes. Preferred ligands include an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; each of which is incorporated herein by reference and other similar materials including 3,5-di-tert-butyl4-hydroxy-N-isobutyl-benzamide, 8-O-acetylharpagide, and the like.

In a preferred embodiment, the ligand for use in the method of modulating expression of gene is a compound of the fortnula:

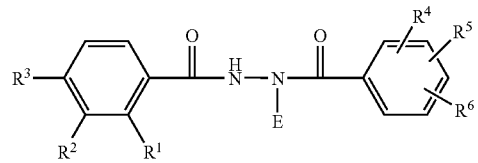

wherein:
E is a $(C_4-C_6)$alkyl containing a tertiary carbon or a cyano $(C_3-C_5)$alkyl containing a tertiary carbon;
$R^1$ is H, Me, Et, i-Pr, F, formyl, $CF_3$, $CHF_2$, $CHCl_2$, $CH_2F$, $CH_2Cl$, $CH_2OH$, $CH_2OMe$, $CH_2CN$, CN, $C°CH$, 1-propynyl, 2-propynyl, vinyl, OH, OMe, OEt, cyclopropyl, $CF_2CF_3$, CH=CHCN, allyl, azido, SCN, or $SCHF_2$;
$R^2$ is H, Me, Et, n-Pr, i-Pr, formyl, $CF_3$, $CHF_2$, $CHCl_2$, $CH_2F$, $CH_2Cl$, $CH_2OH$, $CH_2OMe$, $CH_2CN$, CN, $C°CH$, 1-propynyl, 2-propynyl, vinyl, Ac, F, Cl, OH, OMe, OEt, O-n-Pr, OAc, $NMe_2$, $NEt_2$, SMe, SEt, $SOCF_3$, $OCF_2CF_2H$, COEt, cyclopropyl, $CF_2CF_3$, CH=CHCN, allyl, azido, $OCF_3$, $OCHF_2$, O-i-Pr, SCN, $SCHF_2$, SOMe, NH—CN, or joined with $R^3$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;
$R^3$ is H, Et, or joined with $R^2$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;
$R^4$, $R^5$, and $R^6$ are independently H, Me, Et, F, Cl, Br, formyl, $CF_3$, $CHF_2$, $CHCl_2$, $CH_2F$, $CH_2Cl$, $CH_2OH$, CN, $C°CH$, 1-propynyl, 2-propynyl, vinyl, OMe, OEt, SMe, or SEt.

In another preferred embodiment, the ligand for use in the method of modulating expression of gene is an ecdysone, 20-hydroxyecdysone, ponasterone A, or muristerone A.

In another preferred embodiment, a second ligand may be used in addition to the first ligand discussed above in the method of modulating expression of a gene. Preferably, this second ligand is 9-cis-retinoic acid or a synthetic analog of retinoic acid.

Screening Assays

Identification and isolation of a polynucleotide encoding a whitefly ecdysone receptor polypeptide of the invention provides for expression of whitefly ecdysone receptor in quantities greater than can be isolated from natural sources, or in indicator cells that are specially engineered to indicate the activity of whitefly ecdysone receptor expressed after transfection or transformation of the cells. Accordingly, in addition to rational design of agonists and antagonists based on the structure of whitefly ecdysone receptor polypeptide, the present invention contemplates an alternative method for identifying specific ligands of whitefly ecdysone receptor using various screening assays known in the art.

Thus, the present invention also relates to methods of screening for a compound that induces or represses transactivation of a whitefly ecdysone receptor polypeptide in a cell by contacting a whitefly ecdysone receptor polypeptide with a candidate molecule and detecting reporter gene activity in the presence of the ligand. Candidate compounds may be either agonists or antagonists of the whitefly ecdysone receptor polypeptide. In a preferred embodiment, the whitefly ecdysone receptor polypeptide is expressed from a polynucleotide in the cell and the transactivation activity (i.e., expression or repression of a reporter gene) or compound binding activity is measured.

In a specific embodiment, the present invention relates to methods of screening for molecules that stimulate or inhibit whitefly ecdysone receptor activity in a cell by contacting a whitefly ecdysone receptor polypeptide with a candidate molecule and detecting whitefly ecdysone receptor activity in the presence of the molecule. Candidate molecules may be either agonists or antagonists of whitefly ecdysone receptor. In a preferred embodiment, the whitefly ecdysone receptor is expressed from a polynucleotide in the cell and the whitefly ecdysone receptor activity measured is by induction of expression or transactivation of a reporter gene. Induction of reporter gene expression can be measured as described herein.

Thus, one aspect of the present invention is a method for selecting molecules or ligands that modulate the activity of a whitefly ecdysone receptor polypeptide. In a specific embodiment, the present invention provides a method for identifying a ligand specific for binding to a ligand binding domain of a whitefly ecdysone receptor comprising
  (a) combining (i) a hybrid polypeptide comprising a whitefly ecdysone receptor ligand binding domain and a DNA binding domain from a steroid hormone nuclear receptor superfamily; and (ii) a polynucleotide encoding a second polypeptide, wherein the polynucleotide is operably linked to a transcriptional control element that is responsive to the DNA binding domain of the hybrid polypeptide;
  (b) exposing the hybrid polypeptide and the polynucleotide of (a) to a compound;
  (c) determining ligand activity of the compound of (b) by determining induction of expression of the second polypeptide; and
  (d) identifying the compound that results in the induction of expression of the second polypeptide.

The present invention is also useful to search for orthogonal ligands and orthogonal receptor-based gene expression systems such as those described in co-pending U.S. application 60/237,446, which is incorporated herein by reference in its entirety.

The ligand binding domain ("LBD") of the ecdysone receptor, specifically binds steroid and non-steroidal agonist ligands, thereby providing a means to screen for new molecules possessing the property of binding with high affinity to the ligand binding domain. Thus, the ligand binding domain of a whitefly ecdysone receptor polypeptide may be used as a reagent to develop a binding assay. On one level, the LBD can be used as an affinity reagent for a batch or in a column selective process, to selectively retain ligands which bind. Alternatively, a functional assay is preferred for its greater sensitivity to ligand-binding. By using a reporter molecule for binding, either through a direct assay for binding, or through an expression or other functional linkage between binding and another function, an assay for binding may be developed. For example, by operable linkage of an easily assayable reporter gene to a controlling element responsive to binding by an ecdysone receptor, and where ligand-binding is functionally linked to protein induction, an extremely sensitive assay for the presence of a ligand or of a receptor results. Such a construct is useful for assaying the presence of 20-hydroxyecdysone is described below. This construct is useful for screening for agonists or antagonists of homopteran ecdysone receptors, in particular, whitefly ecdysone receptors.

As presented herein, a whitefly ecdysone receptor can transactivate gene expression of an ecdysone receptor-based gene expression modulation system. Therefore, agonists of whitefly ecdysone receptor that enhance its ability to transactivate gene expression will be expected to improve its activity in an ecdysone receptor-based gene expression modulation system. Inhibitors (antagonists) of whitefly ecdysone receptor activity are useful to reduce its ability to transactivate an ecdysone receptor-based gene expression modulation system.

Any screening technique known in the art can be used to screen for whitefly ecdysone receptor agonists or antagonists. For example, a suitable cell line expressing both whitefly ecdysone receptor and an ecdysone receptor-based gene expression modulation system, can be transfected with a nucleic acid encoding a marker gene, such as β-galactosidase. Cells are then exposed to a test solution comprising an agonist or antagonist, and then stained for β-galactosidase activity. The presence of more β-gal positive cells relative to control cells not exposed to the test solution is an indication of the presence of a whitefly ecdysone receptor agonist in the test solution. Conversely, the presence of less β-gal positive cells relative to control cells not exposed to the test solution is an indication of the presence of a whitefly ecdysone receptor antagonist in the test solution.

The present invention contemplates screens for small molecule ligands or ligand analogs and mimics, as well as screens for natural ligands that bind to and agonize or antagonize whitefly ecdysone receptor in vivo. For example, natural products libraries can be screened using assays of the invention for molecules that agonize or antagonize whitefly ecdysone receptor activity.

Knowledge of the primary sequence of whitefly ecdysone receptor, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, *Science* 249: 386-390 (1990); Cwirla, et al., *Proc. Natl. Acad. Sci.*, 87: 6378-6382 (1990); Devlin et al., *Science,* 249: 404-406 (1990)], very large libraries can be constructed ($10^6$-$10^8$ chemical entities). A second approach uses primarily chemical methods, of which the Geysen method [Geysen et al., *Molecular Immunology* 23: 709-715 (1986); Geysen et al. *J. Immunologic Method* 102: 259-274 (1987)] and the method of Fodor et al. [*Science* 251: 767-773 (1991)] are examples. Furka et al. [14*th International Congress of Biochemistry*, Volume 5, Abstract FR:013 (1988); Furka, *Int. J. Peptide Protein Res.* 37: 487-493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., *Proc. Natl. Acad. Sci. USA* 90: 10700-4 (1993); Ohlmeyer et al., *Proc. Natl. Acad. Sci. USA* 90: 10922-10926 (1993); Lam et al., International Patent Publication No. WO 92/00252; Kocis et al., International Patent Publication No. WO 9428028, each of which is incorporated herein by reference in its entirety], and the like can be used to screen for whitefly ecdysone receptor ligands according to the present invention.

The screening can be performed with recombinant cells that express the whitefly ecdysone receptor, or alternatively, using purified protein, e.g., produced recombinantly, as described above. For example, labeled, soluble whitefly ecdysone receptor can be used to screen libraries, as described in the foregoing references.

In one embodiment, whitefly ecdysone receptor may be directly labeled. In another embodiment, a labeled secondary reagent may be used to detect binding of a whitefly ecdysone receptor to a molecule of interest, e.g., a molecule attached to a solid phase support. Binding may be detected by in situ formation of a chromophore by an enzyme label. Suitable enzymes include, but are not limited to, alkaline phosphatase and horseradish peroxidase. In a further embodiment, a two-color assay, using two chromogenic substrates with two enzyme labels on different acceptor molecules of interest, may be used. Cross-reactive and singly reactive ligands may be identified with a two-color assay.

Other labels for use in the invention include colored latex beads, magnetic beads, fluorescent labels (e.g., fluorescene isothiocyanate (FITC), phycoerythrin (PE), Texas red (TR), rhodamine, free or chelated lanthanide series salts, especially $Eu^{3+}$, to name a few fluorophores), chemiluminescent molecules, radio-isotopes, or magnetic resonance imaging labels. Two-color assays may be performed with two or more colored latex beads, or fluorophores that emit at different wavelengths. Labeled may be detected visually or by mechanical/optical means. Mechanical/optical means include fluorescence activated sorting, i.e., analogous to FACS, and micromanipulator removal means.

As exemplified herein, the level of a whitefly ecdysone receptor polypeptide can be evaluated by metabolic labeling of the proteins. As the metabolic labeling occurs during in vitro incubation of the tissue biopsy in the presence of culture medium supplemented with [$^{35}$S]-methionine, the level of each of the markers detected may be affected by the in vitro conditions. In addition to metabolic (or biosynthetic) labeling with [$^{35}$S]-methionine, the invention further contemplates labeling with [$^{14}$C]-amino acids and [$^3$H]-amino acids (with the tritium substituted at non-labile positions). Thus, a sample or library of compounds can be directly analyzed after labeling of the proteins therein, e.g. by calorimetric staining using silver, gold, coomassie blue, or amido-schwartz, to mention a few techniques; isotopic labeling, e.g., with [$^{32}$P]-orthophosphate, [$^{125}$I], [$^{131}$I]; fluorescent or chemiluminescent tags; and immunological detection with labeled antibody or specific binding partner of a marker.

Modulating Insect Physiology or Development

The isolation of a whitefly ecdysone receptor provides for isolation or screening of new ligands for receptor binding. Some of these will interfere with, or disrupt, normal insect development. It may sometimes be important to either accelerate or decelerate insect development, for instance, in preparing sterile adults for release. Alternatively, in certain circumstances, a delay or change in the timing of development may be lethal or may dramatically modify the ability of an insect to affect an agricultural crop. Thus, naturally occurring, biodegradable and highly active molecules to disrupt the timing of insect development will result.

The present invention provides a means for disrupting insect development where new ligand agonists or antagonists are discovered. These compounds are prime candidates as agonists or antagonists to interfere with the normal insect development. By application of new analogues of ligands for a whitefly ecdysone receptor, it is possible to modify the normal temporal sequence of developmental events. For example, accelerating insect development will minimize generation time. This may be very important in circumstances where large numbers of insects are desired finally, for instance, in producing sterile males. Alternatively, it may be useful to slow development in a pest infestation, such that the insects reach destructive stages of development only after commercial crops may have passed sensitive stages. In another commercial application, ligands discovered by methods provided by the present invention may be used to artificially maintain insects in a specific developmental stage. The development of larvae may also be accelerated to reach a particular developmental stage in their life cycle earlier than naturally.

Other analogues of ligands for a whitefly ecdysone receptor may be selected which, upon application, may be completely disruptive of normal development, leading to a lethal result and pest control. Indeed, there may be new ligands for a whitefly ecdysone receptor which may be species specific or may exhibit a particularly useful spectrum of effectiveness. The greater specificity of the ligands will allow avoidance of use of non-specific pesticides possessing undesired deleterious ecological side effects. Furthermore, compounds having structures closely analogous to natural compounds may be susceptible to natural mechanisms of biological degradation.

Thus, the present invention also provides a method for identifying and selecting compounds exhibiting specific binding to the ligand binding domain to modulate insect physiology or development (e.g., killing) comprising the steps of screening compounds for binding to a homopteran ecdysone receptor, selecting compounds exhibiting said binding and administering the ligand to a homopteran insect. In a specific embodiment, a method for modulating insect physiology or development comprises the steps of screening compounds for binding to a whitefly ecdysone receptor, selecting compounds exhibiting said binding and administering the ligand to a whitefly.

Polypeptide Production

A purified whitefly ecdysone receptor polypeptide of the invention is also useful in a method for determining the structural and biosynthetic aspects of the purified whitefly ecdysone receptor polypeptide. Structural studies of interactions of the ligand-binding domains with selected ligands may be performed by various methods. The preferred method for structural determination is X-ray crystallography but may include various other forms of spectroscopy or chromatography. See, e.g., Connolly, M. L., J. Appl. Crystall. 16: 548 (1983); and Connolly, M. L., Science 221: 709 (1983), which are hereby incorporated herein by reference. For example, the structure of the interaction between ligand and ligand-binding domain may be determined to high resolution.

Having provided for the substantially pure polypeptides, biologically active fragments thereof and recombinant polynucleotides encoding them, the present invention also provides cells comprising each of them. By appropriate introduction techniques well known in the field, cells comprising them may be produced. See, e.g., Sambrook et al. (1989).

Host Cells and Non-Human Organisms

Another aspect of the present invention involves cells comprising an isolated polynucleotide encoding a whitefly ecdysone receptor polypeptide of the present invention. In a specific embodiment, the invention relates to an isolated host cell comprising a vector comprising a polynucleotide encoding a whitefly ecdysone receptor polypeptide of the present invention. The present invention also relates to an isolated host cell comprising an expression vector according to the invention. In another specific embodiment, the invention relates to an isolated host cell comprising a gene expression cassette comprising a polynucleotide encoding a whitefly ecdysone receptor polypeptide of the present invention. In another specific embodiment, the invention relates to an isolated host cell transfected with a gene expression modulation system comprising a polynucleotide encoding a whitefly ecdysone receptor polypeptide of the present invention. In another specific embodiment, the invention also provides an isolated host cell comprising an ecdysone receptor-based gene expression system comprising a whitefly ecdysone receptor polypeptide according to the invention. In another specific embodiment, the invention relates to an isolated host cell comprising a whitefly ecdysone receptor polypeptide of the present invention. In still another embodiment, the invention relates to a method for producing a whitefly ecdysone receptor polypeptide, wherein the method comprises culturing an isolated host cell comprising a polynucleotide encoding a whitefly ecdysone receptor polypeptide of the present invention in culture medium under conditions permitting expression of the polynucleotide encoding the whitefly ecdysone receptor polypeptide, and isolating the whitefly ecdysone receptor polypeptide from the culture.

As described above, the polypeptides of the present invention and the polynucleotides encoding them may be used to modulate gene expression in a host cell. Expression in transgenic host cells may be useful for the expression of various genes of interest. Applicants' invention provides for modulation of gene expression in prokaryotic and eukaryotic host cells. Expression in transgenic host cells is useful for the expression of various polypeptides of interest including but not limited to antigens produced in plants as vaccines, enzymes like alpha-amylase, phytase, glucanase, xylase and xylanase, genes for resistance against insects, nematodes, fungi, bacteria, viruses, and abiotic stresses, antigens, nutraceuticals, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, therapeutic polypeptides, pathway intermediates; for the modulation of pathways already existing in the host for the synthesis of new products heretofore not possible using the host; cell based assays; functional genomics assays, biotherapeutic protein production, proteomics assays, and the like. Additionally the gene products may be useful for conferring higher growth yields of the host or for enabling an alternative growth mode to be utilized.

In a specific embodiment, the isolated host cell is a prokaryotic host cell or a eukaryotic host cell. In another specific embodiment, the isolated host cell is an invertebrate host cell or a vertebrate host cell. Preferably, the isolated host cell is selected from the group consisting of a bacterial cell, a fungal cell, a yeast cell, a nematode cell, an insect cell, a fish cell, a plant cell, an avian cell, an animal cell, and a mammalian cell. More preferably, the isolated host cell is a yeast cell, a nematode cell, an insect cell, a plant cell, a zebrafish cell, a chicken cell, a hamster cell, a mouse cell, a rat cell, a rabbit cell, a cat cell, a dog cell, a bovine cell, a goat cell, a cow cell, a pig cell, a horse cell, a sheep cell, a simian cell, a monkey cell, a chimpanzee cell, or a human cell.

Examples of preferred host cells include, but are not limited to, fungal or yeast species such as *Aspergillus, Trichoderma, Saccharomyces, Pichia, Candida, Hansenula*, or bacterial species such as those in the genera *Synechocystis, Synechococcus, Salmonella, Bacillus, Acinetobacter, Rhodococcus, Streptomyces, Escherichia, Pseudomonas, Metylomonas, Methylobacter, Alcaligenes, Synechocystis, Anabaena, Thiobacillus, Methanobacterium* and *Klebsiella*; plant species selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat; animal; and mammalian host cells.

In a specific embodiment, the isolated host cell is a yeast cell selected from the group consisting of a *Saccharomyces*, a *Pichia*, and a *Candida* host cell.

In another specific embodiment, the isolated host cell is a *Caenorhabdus elegans* nematode cell.

In another specific embodiment, the isolated host cell is a plant cell selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat cell.

In another specific embodiment, the isolated host cell is a zebrafish cell.

In another specific embodiment, the isolated host cell is a chicken cell.

In another specific embodiment, the isolated host cell is a mammalian cell selected from the group consisting of a hamster cell, a mouse cell, a rat cell, a rabbit cell, a cat cell, a dog cell, a bovine cell, a goat cell, a cow cell, a pig cell, a horse cell, a sheep cell, a monkey cell, a chimpanzee cell, and a human cell.

Host cell transformation is well known in the art and may be achieved by a variety of methods including but not limited to electroporation, viral infection, plasmid/vector transfection, non-viral vector mediated transfection, *Agrobacterium*-mediated transformation, particle bombardment, and the like. Expression of desired gene products involves culturing the transformed host cells under suitable conditions and inducing expression of the transformed gene. Culture conditions and gene expression protocols in prokaryotic and eukaryotic cells are well known in the art (see General Methods section of Examples). Cells may be harvested and the gene products isolated according to protocols specific for the gene product.

In addition, a host cell may be chosen that modulates the expression of the transfected polynucleotide, or modifies and processes the polypeptide product in a specific fashion desired. Different host cells have characteristic and specific mechanisms for the translational and post-translational processing and modification [e.g., glycosylation, cleavage (e.g., of signal sequence)] of proteins. Appropriate cell lines or host systems can be chosen to ensure the desired modification and processing of the foreign protein expressed. For example, expression in a bacterial system can be used to produce a non-glycosylated core protein product. However, a polypeptide expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the polypeptide's activity. Furthermore, different vector/host expression systems may affect processing reactions, such as proteolytic cleavages, to a different extent.

Applicants' invention also relates to a non-human organism comprising an isolated host cell according to the invention. In a specific embodiment, the non-human organism is a prokaryotic organism or a eukaryotic organism. In another specific embodiment, the non-human organism is an invertebrate organism or a vertebrate organism.

Preferably, the non-human organism is selected from the group consisting of a bacterium, a fungus, a yeast, a nematode, an insect, a fish, a plant, a bird, an animal, and a mammal. More preferably, the non-human organism is a yeast, a nematode, an insect, a plant, a zebrafish, a chicken, a hamster, a mouse, a rat, a rabbit, a cat, a dog, a bovine, a goat, a cow, a pig, a horse, a sheep, a simian, a monkey, or a chimpanzee.

In a specific embodiment, the non-human organism is a yeast selected from the group consisting of *Saccharomyces*, *Pichia*, and *Candida*.

In another specific embodiment, the non-human organism is a *Caenorhabdus elegans* nematode.

In another specific embodiment, the non-human organism is a plant selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat.

In another specific embodiment, the non-human organism is a *Mus musculus* mouse.

Measuring Gene Expression/Transcription

One useful measurement of the methods of modulating gene expression using the novel polynucleotides, polypeptides, vectors, and/or gene expression cassettes of the present invention is that of the transcriptional state of the cell including the identities and abundances of RNA, preferably mRNA species. Such measurements are conveniently conducted by measuring cDNA abundances by any of several existing gene expression technologies.

Nucleic acid array technology is a useful technique for determining differential mRNA expression. Such technology includes, for example, oligonucleotide chips and DNA microarrays. These techniques rely on DNA fragments or oligonucleotides which correspond to different genes or cDNAs which are immobilized on a solid support and hybridized to probes prepared from total mRNA pools extracted from cells, tissues, or whole organisms and converted to cDNA. Oligonucleotide chips are arrays of oligonucleotides synthesized on a substrate using photolithographic techniques. Chips have been produced which can analyze for up to 1700 genes. DNA microarrays are arrays of DNA samples, typically PCR products, that are robotically printed onto a microscope slide. Each gene is analyzed by a full-or partial-length target DNA sequence. Microarrays with up to 10,000 genes are now routinely prepared commercially. The primary difference between these two techniques is that oligonucleotide chips typically utilize 25-mer oligonucleotides which allow fractionation of short DNA molecules whereas the larger DNA targets of microarrays, approximately 1000 base pairs, may provide more sensitivity in fractionating complex DNA mixtures.

Another useful measurement of Applicants' methods of the invention is that of determining the translation state of the cell by measuring the abundances of the constituent protein species present in the cell using processes well known in the art.

Where identification of genes associated with various physiological functions is desired, an assay may be employed in which changes in such functions as cell growth, apoptosis, senescence, differentiation, adhesion, binding to a specific molecules, binding to another cell, cellular organization, organogenesis, intracellular transport, transport facilitation, energy conversion, metabolism, myogenesis, neurogenesis, and/or hematopoiesis is measured.

In addition, selectable marker or reporter gene expression may be used to measure gene expression modulation using Applicants' invention.

Other methods to detect the products of gene expression are well known in the art and include Southern blots (DNA detection), dot or slot blots (DNA, RNA), northern blots (RNA), RT-PCR(RNA), western blots (polypeptide detection), and ELISA (polypeptide) analyses. Although less preferred, labeled proteins can be used to detect a particular nucleic acid sequence to which it hybridizes.

In some cases it is necessary to amplify the amount of a nucleic acid sequence. This may be carried out using one or more of a number of suitable methods including, for example, polymerase chain reaction ("PCR"), ligase chain reaction ("LCR"), strand displacement amplification ("SDA"), transcription-based amplification, and the like. PCR is carried out in accordance with known techniques in which, for example, a nucleic acid sample is treated in the presence of a heat stable DNA polymerase, under hybridizing conditions, with one pair of oligonucleotide primers, with one primer hybridizing to one strand (template) of the specific sequence to be detected. The primers are sufficiently complementary to each template strand of the specific sequence to hybridize therewith. An extension product of each primer is synthesized and is complementary to the nucleic acid template strand to which it hybridized. The extension product synthesized from each primer can also serve as a template for further synthesis of extension products using the same primers. Following a sufficient number of rounds of synthesis of extension products, the sample may be analyzed as described above to assess whether the sequence or sequences to be detected are present.

The present invention may be better understood by reference to the following non-limiting Examples, which are provided as exemplary of the invention.

EXAMPLES

General Molecular Biology Techniques

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Conventional cloning vehicles include pBR322 and pUC type plasmids and phages of the M13 series. These may be obtained commercially (Bethesda Research Laboratories).

For ligation, DNA fragments may be separated according to their size by agarose or acrylamide gel electrophoresis, extracted with phenol or with a phenol/chloroform mixture, precipitated with ethanol and then incubated in the presence of phage T4 DNA ligase (Biolabs) according to the supplier's recommendations.

The filling in of 5' protruding ends may be performed with the Klenow fragment of *E. coli* DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

Mutagenesis directed in vitro by synthetic oligodeoxynucleotides may be performed according to the method developed by Taylor et al. [Nucleic Acids Res. 13 (1985) 8749-8764] using the kit distributed by Amersham.

The enzymatic amplification of DNA fragments by PCR [Polymerase-catalyzed Chain Reaction, Saiki R. K. et al., Science 230 (1985) 1350-1354; Mullis K. B. and Faloona F. A., Meth. Enzym. 155 (1987) 335-350] technique may be performed using a "DNA thermal cycler" (Perkin Elmer Cetus) according to the manufacturer's specifications.

Verification of nucleotide sequences may be performed by the method developed by Sanger et al. [Proc. Natl. Acad. Sci. USA 74: 5463-5467 (1977)] using the kit distributed by Amersham.

Plasmid DNAs may be purified by the Qiagen Plasmid Purification System according to the manufacture's instruction.

Example 1

This Example describes the cloning of full-length cDNA encoding whitefly *Bamecia argentifoli* ecdysone receptor polypeptide. To isolate the full length coding sequence of this previously unknown whitefly ecdysone receptor isoform (herein named "BaEcR"), a whitefly cDNA library prepared from total RNA obtained from mixed stage whitefly nymphs (first to fourth instars) and pupa was used. Briefly, the cDNA library was constructed in the UNI-Zap XR™ vector using Zap Express cDNA Gigapack II Gold™ cloning kit (Stratagene, La Jolla, Calif.) following the manufacturer's instructions. Applicants used degenerate oligonucleotides (see Table 2; SEQ ID NOs: 3 and 4) designed based on conserved regions of ecdysone receptor C (KKCLSVGM; SEQ ID NO: 5) and E (KLIREDQI; SEQ ID NO: 6) domains to amplify and obtain a 441 base pair (bp) cDNA fragment (SEQ ID NO: 7) from whitefly total RNA using RT-PCR.

| Primer and SEQ ID NO: | Primer Nucleic Acid Sequence |
|---|---|
| Primer 1 (SEQ ID NO: 3) | 5'-aa(a/g)aa(a/g)tg(t/c)ct(t/c/a/g)ag(t/c)gt(t/c/a/g)gg(t/c/a/g)atg-3' |
| Primer 2 (SEQ ID NO: 4) | 5'-(a/g/t)at(t/c)tg(a/g)tc(t/c)tc(t/a/c/g)cg(a/g/t)at(t/c/a/g)ag(t/c)tt-3' |

Reverse transcription was performed by THERMO-SCRIPT RT-PCR System (LifeTechnologies). Polymerase chain reaction (PCR) amplification was performed using the TaqPlus polymerase (Stratagene) and the reaction conditions and cycling parameters as follows. PCR was performed using 1× reaction buffer (Stratagene), 50 ng of dsDNA template, 125 ng of forward primer (Primer 1), 125 ng of reverse complementary primer (Primer 2), and 1 µl of dNTP mix (LifeTechnologies) in a final reaction volume of 50 µL. The cycling parameters used consisted of 35 cycles of denaturing at 95° C. for 1 minute, annealing at 55° C. for 50 seconds, and extending at 72° C. for 50 seconds, followed by a final elongation cycle at 72° C. for 10 minutes.

The resulting 441 bp cDNA fragment (SEQ ID NO: 7) was then used as a probe to screen the whitefly cDNA library following high stringency hybridization and washing protocols for the full length BaEcR cDNA clone. The hybridization conditions and phage infection methods were performed according to the manufacturer's instructions in the Zap Express cDNA Gigapack II Gold™ cloning kit (Stratagene, La Jolla, Calif.) and as recommended by Maniatis et al., supra. One positive clone was isolated, purified, in-vivo excised, and both strands of its corresponding whitefly cDNA insert sequenced using standard protocols (see Maniatis et al., supra).

The polynucleotide sequence of this isolated cDNA clone, which encodes the full length BaEcR, is presented as SEQ ID NO: 1. The deduced amino acid sequence of the full length BaEcR is presented herein as SEQ ID NO: 2 and showed high similarity with the deduced amino acid sequence of other EcRs (data not shown).

Example 2

This Example describes the construction of whitefly ecdysone receptor gene expression cassettes and their use in an ecdysone receptor-based gene expression modulation system. The results presented herein demonstrate that a whitefly ecdysone receptor is functional in an ecdysone receptor-based gene expression modulation system in both insect and mammalian cells.

A) Insect Cells:

Briefly, the BaEcR CDE domains (amino acids 53-416 of SEQ ID NO: 2) were fused to a VP16 transactivation domain (SEQ ID NO: 8) as follows. A construct was prepared by fusing a polynucleotide (nucleotides 259-1349 of SEQ ID NO: 1) encoding a BaEcR-CDE polypeptide to a polynucleotide (SEQ ID NO: 9) encoding a VP16 activation domain at the NH2 terminal end. This VP16BaEcR fusion was then cloned under the control of baculovirus IE1 promoter (SEQ ID NO: 10). The VP16BaEcR gene expression cassette was transfected into L57 cell line (*Drosophila* cell line that lacks endogenous EcR) and a cotton boll weevil ("CBW"; *Anthonomus grandis*) BRL-AG-2 cell line (generously provided by USDA, ARS, Bioscience Research Laboratory, Fargo, N. Dak.) along with a reporter construct EcRELaCZ that comprises a 6×ECRE response element (1×EcRE is shown in SEQ ID NO: 11), an ADH distal promoter (see Heberlein et al., 1985, Cell 41: 965-977 and Koelle et al. 1991, Cell 67: 59-77) and a LacZ reporter gene (SEQ ID NO: 12). The reporter gene activity was quantified in the presence of 0, 0.0001, 0.001, 0.01, 0.1, 1, 10, and 100 µM 20-hydroxyecdysone (20E) ligand or N-(2-ethyl-3-methoxybenzoyl)-N'-(3,5-dimethylbenzoyl)-N'-tert-butylhydrazine (GS™-E) ligand.

Ligands: The steroid ligand 20-hydroxyecdysone (20E) was purchased from Sigma Chemical Company. The nonsteroidal ligand N-(2-ethyl-3-methoxybenzoyl)-N'-(3,5-dimethylbenzoyl)-N'-tert-butylhydrazine (GS™-E) is a synthetic stable ecdysteroid ligand that was synthesized at Rohm and Haas Company. The ligands were dissolved in DMSO and the final concentration of DMSO was maintained at 0.1% in both controls and treatments.

Transfections: DNAs corresponding to the gene constructs described above were transfected into L57 or the CBW cells as follows. L57 cells were grown in HyQ-CCM3 medium (Hyclone labs) and transfected with lipofectomine (Life Technologies). The CBW cells were grown in Ex-Cell 401 (JRH Sciences) and transfected with Celfectin (Invitrogen). Standard methods for culture and maintenance of the cells were followed. Cells were harvested when they reached 50% confluency and plated in 6-, 12- or 24-well plates at 125,000, 50,000, or 25,000 cells, respectively, in 2.5, 1.0, or 0.5 ml of growth medium, respectively. The next day, the cells were rinsed with growth medium and transfected for four hours. For 12-well plates, 4 µl of the appropriate transfection reagent was mixed with 100 µl of growth medium One µg of reporter construct and 0.25 µg of each receptor construct of the receptor pair to be analyzed were added to the transfection mix. A second reporter construct was added [pTKRL (Promega), 0.1 µg transfection mix] that comprises a *Renilla* luciferase gene operably linked and placed under the control of a thymidine kinase (TK) constitutive promoter and was used for normalization. The contents of the transfection mix were mixed in a vortex mixer and let stand at room temperature for 30 minutes. At the end of incubation, the transfection mix was added to the cells maintained in 400 µl growth medium. The cells were maintained at 37° C. and 5% $CO_2$ for four hours. At the end of incubation, 500 µl of growth medium and either dimethylsulfoxide (DMSO; control) or a DMSO solution of steroidal ligand or non-steroidal ligand was added and the cells were maintained at 37° C. and 5% $CO_2$ for 48 hours. The cells were harvested and reporter activity was assayed. The same procedure was followed for 6 and 24 well plates as well except all the reagents were doubled for 6 well plates and reduced to half for 24-well plates.

Reporter Assays: Cells were harvested 48 hours after adding ligand. 125 µl of passive lysis buffer (part of Dual-luciferase™ reporter assay system from Promega Corporation) were added to each well of the 24-well plate. The plates were placed on a rotary shaker for 15 minutes. Twenty µl of lysate were assayed. Luciferase activity was measured using Dual-luciferase™ reporter assay system from Promega Corporation following the manufacturer's instructions. β-Galactosidase was measured using Galacto-Star™ assay kit from TROPIX following the manufacturer's instructions. All luciferase and β-galactosidase activities were normalized using *Renilla* luciferase as a standard. Fold activities were calculated by dividing normalized relative light units ("RLU") in ligand treated cells with normalized RLU in DMSO treated cells (untreated control). The results are presented in FIG. 1 and the numbers on the top of each bar show the maximum fold induction for that group.

As shown in FIG. 1, the BaEcR construct was able to transactivate reporter gene activity in a dose-dependent manner with both ligands tested in the CBW cells. However, in L57cells there was very little transactivation in the presence of either ligand. Applicants' previous studies have shown that both CfEcR and DmEcR cause good transactivation in L57 but BaEcR was a poor transactivator in these cells.

B) Mammalian Cells:

Briefly, the BaEcR DE domains (amino acids 119-416 of SEQ ID NO: 2) were fused to a GAL4 DNA binding domain (SEQ ID NO: 13) as follows. A construct was prepared by fusing a polynucleotide (nucleotides 458-1349 of SEQ ID NO: 1) encoding a BaEcR-DE polypeptide to a polynucleotide (SEQ ID NO: 14) encoding a GAL4 DNA-binding domain at the NH2 terminal end. This GAL4/BaEcR fusion was then cloned under the control of a cytomegalovirus (CMV) promoter/enhancer (SEQ ID NO: 15). In addition, a polynucleotide encoding the EF domains of seven RXR/USPs from a moth *Choristoneura fumifeiana* ultraspiracle protein ("CfUSP", SEQ ID NO: 16), a fruit fly *Drosophila melanogaster* ultraspiracle protein ("DmUSP"; SEQ ID NO: 17), a locust *Locusta migratoria* ultraspiracle protein (LmUSP; SEQ ID NO: 18), a mouse *Mus musculus* retinoid X receptor isoform α (MmRXRα; SEQ ID NO: 19), a chimeric RXR/USP between MmRXRα and LmUSP (Chimera; SEQ ID NO: 20), a tick *Amblyomma americanum* retinoid X receptor homolog 1 (AmaRXR1; SEQ ID NO: 21), and a tick *Amblyomma americanum* retinoid X receptor homolog 2(AmaRXR2; SEQ ID NO: 22) were each fused to a polynucleotide (SEQ ID NO: 9) encoding a VP16 activation domain.

The GAL4/BaEcR gene expression cassette was transfected into NIH3T3 cells (ATCC) along with each of the seven VP16RXR/USP gene expression cassettes and a reporter construct pFRLuc that comprises a 5×GAL4RE (1×GAL4RE is shown in SEQ ID NO: 23), a synthetic TATA (SEQ ID NO: 24) and a luciferase reporter gene (SEQ ID NO: 25) as described above except the cells were cultured in growth media comprising 10% fetal bovine serum (FBS), Superfect™ (Qiagen Inc.) was used as the transfection reagent, and at the end of incubation/transfection, 500 µl of growth medium containing 20% FBS was added to the cells.

The receptor combinations were compared for their ability to transactivate pFRLuc in NIH3T3 cells in the presence of 0, 0.2, 1.0, or 10 µM steroid ponasteroneA (PonA; Invitrogen) or 0, 0.04, 0.2, 1.0, or 10 µM GS™-E. The ligands were dissolved in DMSO and the final concentration of DMSO was maintained at 0.1% in both controls and treatments. The results are presented in FIG. 2 and the numbers on the top of each bar show the maximum fold induction for that group.

Figure 2:
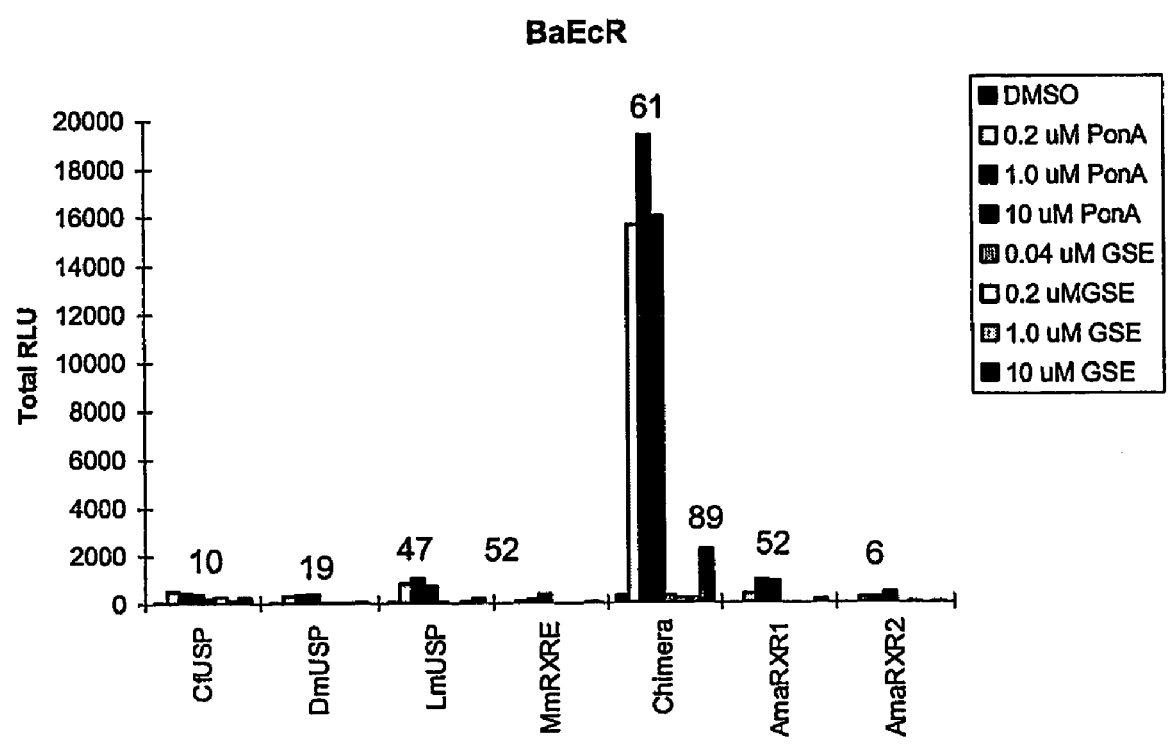
FIG. 2: Transactivation of reporter genes through GAL4/BaEcR-DE construct transfected into NIH3T3 cells along with VP16/CfUSP-EF, VP16/DmUSP-EF, VP16/MmRXRα-EF, VP16/MmRXRα/LmUSP-EF chimera, VP16/Ama-RXR1-EF, or VP16/AmaRX2-EF, and pFRLuc by PonA or GS™-E. The numbers on top of the bars indicate the maximum fold induction for that group.

As shown in FIG. 2, BaEcR in combination with any of the RXR/USP receptor constructs tested induced reporter gene activity, indicating that BaEcR is functional in mammalian cells.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

We claim:

1. An isolated polynucleotide comprising a nucleic acid sequence selected from the group consisting of SEQ ID NO: 1, nucleotides 102-1349 of SEQ ID NO: 1, nucleotides 102-258 of SEQ ID NO: 1, nucleotides 259-457 of SEQ ID NO: 1, nucleotides 458-677 of SEQ ID NO: 1, nucleotides 678-1349 of SEQ ID NO: 1, nucleotides 259-1349 of SEQ ID NO: 1, nucleotides 458-1349 of SEQ ID NO: 1, and nucleotides 648-1349 of SEQ ID NO: 1.

2. An isolated polynucleotide encoding a polypeptide comprising an amino acid sequence selected from the group consisting of SEQ ID NO: 2, amino acids 1-52 of SEQ ID NO: 2, amino acids 119-192 of SEQ ID NO: 2, amino acids 193-416 of SEQ ID NO: 2, amino acids 53-416 of SEQ ID NO: 2, amino acids 119-416 of SEQ ID NO: 2, and amino acids 183-416 of SEQ ID NO: 2.

3. A vector comprising the isolated polynucleotide according to claims 1 or 2.

4. The vector according to claim 3, wherein the isolated polynucleotide is operatively linked to an expression control sequence that permits expression of the isolated polynucleotide in an expression competent host cell.

5. The vector according to claim 4, wherein the expression control sequence comprises a promoter that is functional in a mammalian cell.

6. The vector according to claim 4, wherein the vector is selected from the group consisting of an RNA molecule, a plasmid, and a viral vector.

7. The vector according to claim 6, wherein the vector is a plasmid.

8. An isolated host cell transfected with the vector according to claim 3.

9. The isolated host cell according to claim 8, wherein the host cell is selected from the group consisting of a bacterial cell, a fungal cell, a yeast cell, a nematode cell, an insect cell, a fish cell, a plant cell, an avian cell, an animal cell, and a mammalian cell.

10. A method for producing a whitefly ecdysone receptor polypeptide comprising:
    a) culturing the host cell of claim 8 in culture medium under conditions permitting expression of a whitefly ecdysone receptor polypeptide; and
    b) isolating the whitefly ecdysone receptor polypeptide from the culture medium.

11. A composition comprising the isolated polynucleotide according to claims 1 or 2 and an acceptable carrier.

12. A composition comprising the vector according to claim 3 and an acceptable carrier.

* * * * *